United States Patent [19]

Drew et al.

[11] Patent Number: 5,313,061
[45] Date of Patent: May 17, 1994

[54] MINIATURIZED MASS SPECTROMETER SYSTEM

[75] Inventors: Russell C. Drew, Great Falls; Thomas J. Kuehn, Sterling, both of Va.

[73] Assignee: Viking Instrument, Reston, Va.

[21] Appl. No.: 803,794

[22] Filed: Dec. 6, 1991

Related U.S. Application Data

[63] Continuation of Ser. No. 714,981, Jun. 14, 1991, abandoned, which is a continuation of Ser. No. 362,287, Jun. 6, 1989, abandoned.

[51] Int. Cl.⁵ ............................................. H01J 49/26
[52] U.S. Cl. .................................. 250/281; 250/296; 250/298; 250/288
[58] Field of Search .................... 250/281, 282, 423 R, 250/296, 298, 294, 346 R, 346 ML, 288, 288 A, 294, 289; 313/268, 451, 417

[56] References Cited

U.S. PATENT DOCUMENTS

| | | | |
|---|---|---|---|
| H414 | 1/1988 | Young et al. | 250/423 R |
| 2,916,649 | 12/1959 | Levin | 313/250 |
| 3,084,249 | 4/1963 | Enge | 250/281 |
| 3,230,362 | 1/1966 | Davis et al. | 250/281 |
| 3,291,980 | 12/1966 | Coates et al. | 250/288 A |
| 3,594,574 | 7/1971 | Morgan et al. | 250/281 |
| 3,659,236 | 4/1972 | Whitehead, Jr. | 250/281 |
| 3,699,332 | 10/1972 | Hull et al. | 250/396 R |
| 3,700,893 | 10/1972 | Seidenberg et al. | 250/281 |
| 3,939,344 | 2/1976 | McKinney | 250/281 |
| 3,946,227 | 3/1976 | Bingham | 250/281 |
| 3,984,692 | 10/1976 | Arsenault | 250/423 R |
| 3,992,626 | 11/1976 | Bursack | 250/289 |
| 3,996,464 | 12/1976 | Fletcher et al. | 250/289 |
| 4,008,388 | 2/1977 | McLafferty et al. | 250/281 |
| 4,016,421 | 4/1977 | Hull et al. | 250/423 R |
| 4,037,100 | 7/1977 | Purser | 250/281 |
| 4,160,161 | 7/1979 | Horton | 250/288 A |
| 4,209,696 | 6/1980 | Fite | 250/281 |
| 4,213,326 | 7/1980 | Brodasky | 250/288 A |
| 4,256,963 | 3/1981 | Takahashi et al. | 250/281 |
| 4,266,127 | 5/1981 | Chang | 250/281 |
| 4,296,323 | 10/1981 | Gerlach | 250/289 |
| 4,315,153 | 2/1982 | Vahrenkamp | 250/281 |
| 4,411,575 | 10/1983 | Miller | 250/288 |
| 4,442,353 | 4/1984 | Baubron | 250/281 |
| 4,459,481 | 7/1984 | Todd et al. | 250/282 |
| 4,459,844 | 7/1984 | Burkhart | 73/40.7 |
| 4,472,630 | 9/1984 | Schoen | 250/281 |
| 4,472,631 | 9/1984 | Enke et al. | 250/281 |
| 4,480,187 | 10/1984 | Matsuda | 250/296 |
| 4,514,628 | 4/1985 | Frehaut et al. | 250/299 |
| 4,517,461 | 5/1985 | Crandall | 250/288 A |
| 4,536,652 | 8/1985 | Cooks et al. | 250/281 |
| 4,560,878 | 12/1985 | Knauer et al. | 250/396 R |
| 4,652,752 | 3/1987 | Ino et al. | 250/281 |
| 4,686,365 | 8/1987 | Meek et al. | 250/281 |
| 4,694,168 | 9/1987 | Le Beyec et al. | 250/281 |
| 4,723,076 | 2/1988 | Bateman | 250/296 |
| 4,746,794 | 5/1988 | French et al. | 250/281 |
| 4,812,649 | 3/1989 | Nakagawa | 250/281 |
| 4,842,701 | 6/1989 | Smith et al. | 250/281 |
| 4,851,669 | 7/1989 | Aberth | 250/281 |
| 4,866,267 | 9/1989 | Matsuda et al. | 250/281 |
| 5,012,052 | 4/1991 | Hayes | 250/288 |

FOREIGN PATENT DOCUMENTS

WO89/03585  4/1989  PCT Int'l Appl.

OTHER PUBLICATIONS

J. R. Wyatt, "Development of a Small Magnetic Mass Spectrometer for Atmosphere Analysis/Process Control", *International Journal of Mass Spectrometry and Ion Processes*, vol. 60, No 1 (1984), pp. 289-297.

(List continued on next page.)

*Primary Examiner*—Paul M. Dzierzynski
*Assistant Examiner*—Kiet T. Nguyen
*Attorney, Agent, or Firm*—Dickstein, Shapiro & Morin

[57] ABSTRACT

A portable analytical grade mass spectrometer system contained in a single enclosure is disclosed for use in analyzing atmospheric, water, soil, drugs, explosives and other substances and includes a gas chromatograph and a mass analyzer assembly enclosed within a vacuum housing, a vacuum pump, and an on-board computer such that an operator, by means of an attached keyboard, can input data and information, and input a sample to be analyzed, and thereby operate the miniaturized mass spectrometer system.

23 Claims, 24 Drawing Sheets

OTHER PUBLICATIONS

D. Rushneck et al., "Viking Gas Chromatograph-Mass Spectrometer", Review of Scientific Instrumentation, vol. 49, No. 6, Jun. 1978, pp. 817-833.

J. Evans and J. Arnold, "Monitoring Organic Vapors", Environmental Science and Technology, vol. 9, No. 13, Dec. 1975, pp. 1134-1138.

Industrial Chemical News, vol. 7, No. 12, Dec. 1986, pp. 13-15 and 25.

A six page brochure for the QAS 100 Gas Analysis manufactured by Leybold AG. Oct. 1987.

A four page brochure for the OAS 100 Mass Spectrometer System from Leybold AG Oct. 1987.

A four page brochure for the ICAMS Atmosphere Monitor from Perkin-Elmer. Dec. 1984.

A six page brochure for the Mobile TAGA 3000 MS and 600 MS/MS from TRC Advanced Analytics, Inc. Oct. 1982.

A seven page brochure for the MS2 Organic Chemical Analysis Laboratory from New York Research Consultants, Inc., 1984.

A seven page brochure for the INOCS 50 Quadrupole Mass Spectrometer from Finnigan Mat. Jun. 1984.

A nine page brochure for the MM-1 Mobile Mass Spectrometer from Bruker Instruments, Inc. Sep. 1986.

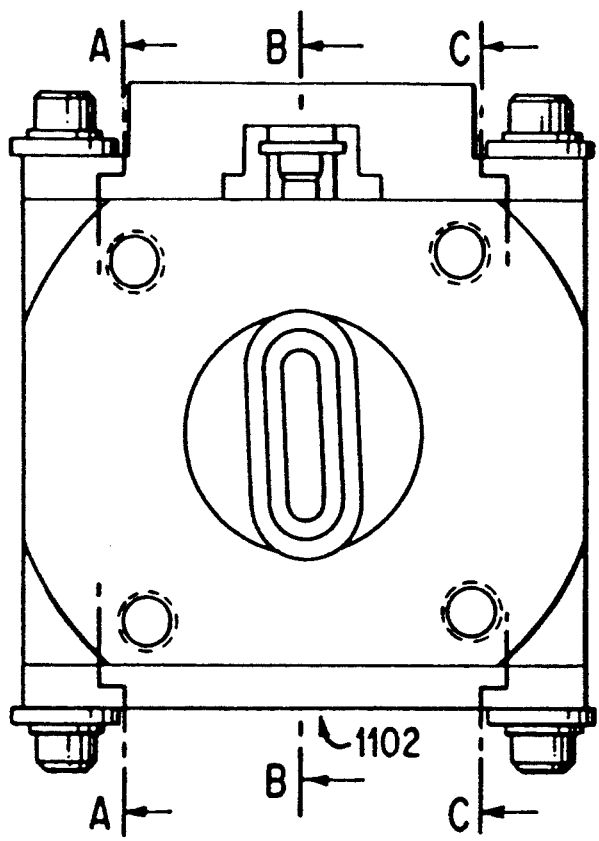
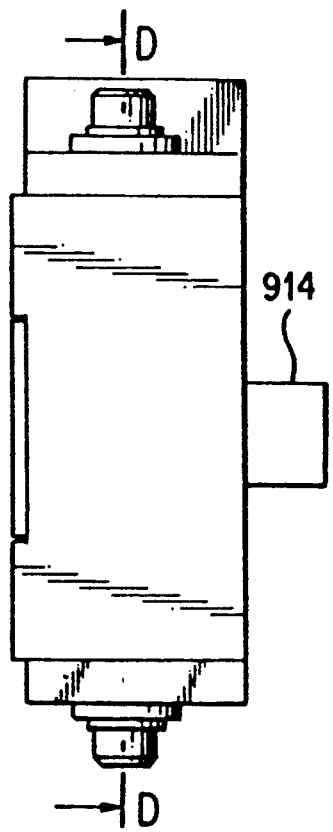
FIG. 11a  FIG. 11b
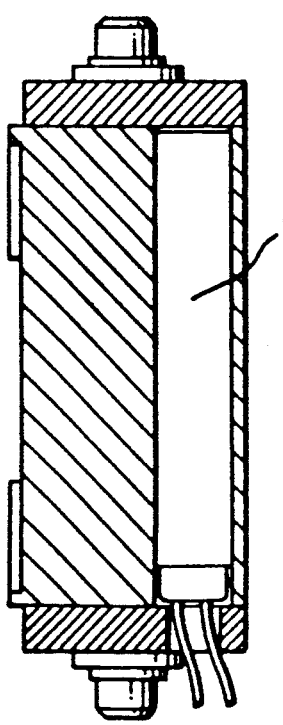
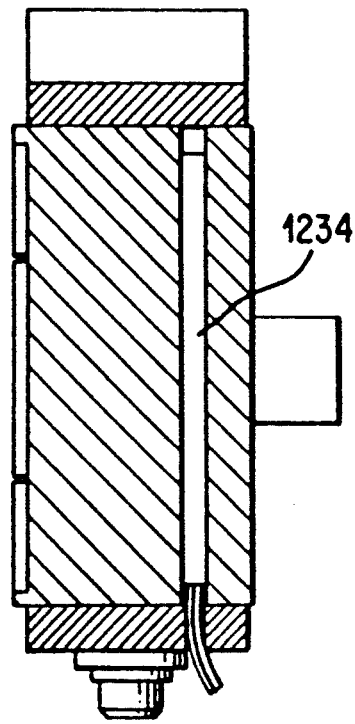
FIG. 11e  FIG. 11f

MINIATURIZED MASS SPECTROMETER SYSTEM

This application is a continuation of application Ser. No. 07/714,981, filed Jun. 14, 1991, now abandoned, which is a continuation of application Ser. No. 362,287, filed Jun. 6, 1989, now abandoned.

BACKGROUND OF THE INVENTION

The present invention relates generally to the determination of the chemical composition of unknown chemical compounds. More particularly, the present invention relates to apparatus for determining the chemical composition of environmental and non-environmental substances, such as hazardous and toxic chemicals, air and water contaminants.

In the area of environmental testing of the composition of the air, water, hazardous chemicals and other environmental as well as non-environmental samples, including the detection of drugs and explosives, it is often desirable and much of the time necessary to conduct the tests of such materials at the source or location of the materials. Since such materials are oftentimes found outside of controlled environments which are provided with sources of power, and since it is often important, for example, in the case of drugs and explosives, to quickly ascertain the presence of such substances in a rapid manner in the absence of readily available power sources, the need has arisen in the art for a compact, powerful and yet very sensitive instrument for testing as well as monitoring the chemical composition of such materials.

With many presently available systems, it takes days and often weeks to transport the samples to a central laboratory and obtain the results from the sophisticated routines necessary to analyze the chemical composition of certain substances. The present invention, on the other hand, both senses and analyzes such substances in minutes right on the site where the substance is found. In addition to providing advanced field testing and analysis, the present invention, which includes a novel gas chromatograph and mass spectrometer combination, provides a comprehensive real-time monitoring and on-site assessment capability for scientists, engineers, compliance specialists and others with environmental protection and public safety responsibilities.

The present system, then, combines in one portable compact package a fully integrated and totally self-contained system which couples a temperature programmed gas chromatograph with a high performance miniaturized mass spectrometer and on-board computer. The computer includes an operating system, as well as a mass spectra library and analysis software.

SUMMARY AND OBJECTS OF THE INVENTION

In view of the foregoing, it should be apparent that there still exists a need in the art for a portable, self-contained and miniaturized substance testing and monitoring system which can be readily brought by one person to a source of materials to be analyzed and can quickly and efficiently perform a chemical analysis of the substance to determine its chemical composition. Such an apparatus could also be installed at a remote site to automatically monitor and analyze chemical pollution by unattended or remotely controlled operation.

It is, therefore, a primary object of this invention to provide apparatus for analyzing unknown substances to determine their chemical composition which is characterized by a compact, lightweight, power efficient, and self-contained yet high performance system using a gas chromatograph and mass spectrometer system operated by an on-board computer and which has particular application for the monitoring of air and water quality, hazardous materials, explosives and drugs.

More particularly, it is an object of this invention to provide a miniaturized gas chromatograph/mass spectrometer (GC/MS) system which is compact, rugged and yet capable of rapidly and efficiently performing an analysis of various samples in near real-time at the site.

Still more particularly, it is an object of this invention to provide a gas chromatograph/mass spectrometer system which is relatively low in cost and is easily manufacturable.

A further object of the present invention is to provide a miniaturized mass spectrometer system utilizing an analytical grade mass spectrometer having a resolution of at least 1 AMU and a mass range of at least 200 AMU.

It is an additional object of the present invention to provide a miniaturized mass spectrometer system which includes an analytical grade mass spectrometer and in which all major components of the entire system, as well as the data processing functions of the system, are contained in a single compact enclosure.

Yet an additional object of the present invention is to provide for a compact, portable and self-contained miniaturized mass spectrometer system which includes an analytical grade mass spectrometer as well as a data processor and microcomputer all in a portable and self-contained compact enclosure together with a display and user input/output device.

It is yet another object of the present invention to provide a miniaturized mass spectrometer system which includes an analytical grade mass spectrometer and a vacuum pump in a single self-contained and portable enclosure.

It is a further object of the present invention to provide a miniaturized mass spectrometer system which provides more than one stage of analytical grade mass spectrometry.

It is a still further object of the present invention to provide a mass analyzer assembly which forms a part of a mass spectrometer inside a vacuum enclosure and in which the alignment of the ion beam is achieved by a single unitary alignment device which aligns two or more of the ion source, electric scanning sectors, magnetic analyzers or ion detection components.

It is another object of the present invention to provide a mass analyzer assembly in which the mechanisms for providing alignment of the sections of the mass analyzer are formed as part of the vacuum housing containing the mass analyzer assembly.

It is yet an additional object of the present invention to provide a mass analyzer assembly with a source of vacuum located inside the vacuum housing which surrounds the mass analyzer assembly.

Still another object of the present invention is to provide a compact magnet and yoke combination which serves the dual function of providing the magnetic field required for both the ion vacuum pump and the magnetic analyzer used in connection with the mass analyzer assembly.

Still yet another object of the present invention is to provide a magnet and yoke structure for the ion pump and magnetic analyzer sections of a mass spectrometer in which a portion of the yoke structure is used to shield part of the ion beam utilized by the mass spectrometer and/or the yoke forms part of the vacuum housing.

It is yet another object of the present invention to provide a novel magnet and yoke structure for use with a mass spectrometer system such that the magnet and yoke system is located outside of the vacuum housing and in which the magnet is formed of a high flux magnetic material so that the magnet may be removed to permit high temperature baked-out of the vacuum housing without overheating the magnet structure.

It still another object of the present invention to provide a novel magnet and yoke structure for use with a mass spectrometer system such that the magnet and yoke system is located inside of the vacuum housing and in which the magnet is formed of a high flux heat, resistant magnetic material such that it can be baked out with the vacuum housing without compromising its magnetic properties.

Another object of the present invention is to provide a reliable, easily aligned and assembled ion source and electric sector assembly for use with a miniaturized gas chromatograph/mass spectrometer system.

Briefly described, these and other objects of the invention are accomplished by providing a miniaturized mass spectrometer system comprised of a sample concentrator, a gas chromatograph, a gas chromatograph-mass spectrometer interface, an analytical grade mass spectrometer, a microcomputer and the electronics and power necessary for operating the system in a compact, self-contained single enclosure which also includes an on-board computer display screen. The mass spectrometer system contained within the total system is capable of achieving a resolution of greater than 1 AMU and a mass range of greater than 200 AMU. The portable mass spectrometer system is contained within a vacuum housing which is initially evacuated to a pressure of about $10^{-4}$ to $10^{-6}$ Torr by an external pump and then is maintained by an internal vacuum pump at that pressure. The vacuum housing is comprised of two or more pieces and a high vacuum seal such that maintenance to the mass analyzer assembly can be readily accomplished. In addition, the vacuum housing may include a mechanism for aligning two or more components of the mass analyzer assembly.

There is also disclosed a novel electric sector structure in which the two sector portions and the electric sector plates are precisely aligned to and insulated from each other by means of precision formed spheres made of a suitable electrically insulating material. A novel ion source is also disclosed which utilizes a series of unitary mounting disks holding precision fabricated lenses. The lenses are separated from each other by electrically insulating spacers and are contained within a housing constructed of ceramic or other insulating and minimally out-gassing materials. That structure is simple and compact yet provides for a reliable method of aligning the lenses while providing electrical isolation between each of the lenses.

A novel appendage magnet and yoke assembly is also disclosed which may be designed to surround a portion of the outside of the vacuum housing and be removable therefrom, such that the vacuum housing can be baked-out without overheating the magnets. In addition, such magnet and yoke structure may be utilized to produce the magnetic fields needed to operate both the ion pump and magnetic analyzer components of the mass spectrometer.

With these and other objects, advantages and features of the invention that may become hereinafter apparent, the nature of the invention may be more clearly understood by reference to the following detailed description of the invention, the appended claims and to the several drawings attached herein.

BRIEF DESCRIPTION OF THE DRAWINGS

FIG. 7b is a drawing of a top view of the magnet assembly of FIG. 7a;

FIG. 11a is a drawing of the top view of the block assembly for use as part of the ion source assembly of the present invention;

FIG. 11b is a drawing of the side view of the block assembly for use as part of the ion source assembly of the present invention;

FIG. 11e is a drawing of a section taken along the line A—A of FIG. 11a of the block assembly of the present invention;

FIG. 11f is a drawing of a section taken along the line C—C of FIG. 11a of the block assembly of the present invention;

FIG. 12b is a drawing of the top and edge views of a first portion of a lens forming element mounted to the disk of FIG. 12a;

FIG. 12c is the drawing of a top and edge views of a second portion of a lens forming element mounted to the disk of FIG. 12a;

DETAILED DESCRIPTION OF THE PREFERRED EMBODIMENT

Figure 1A:
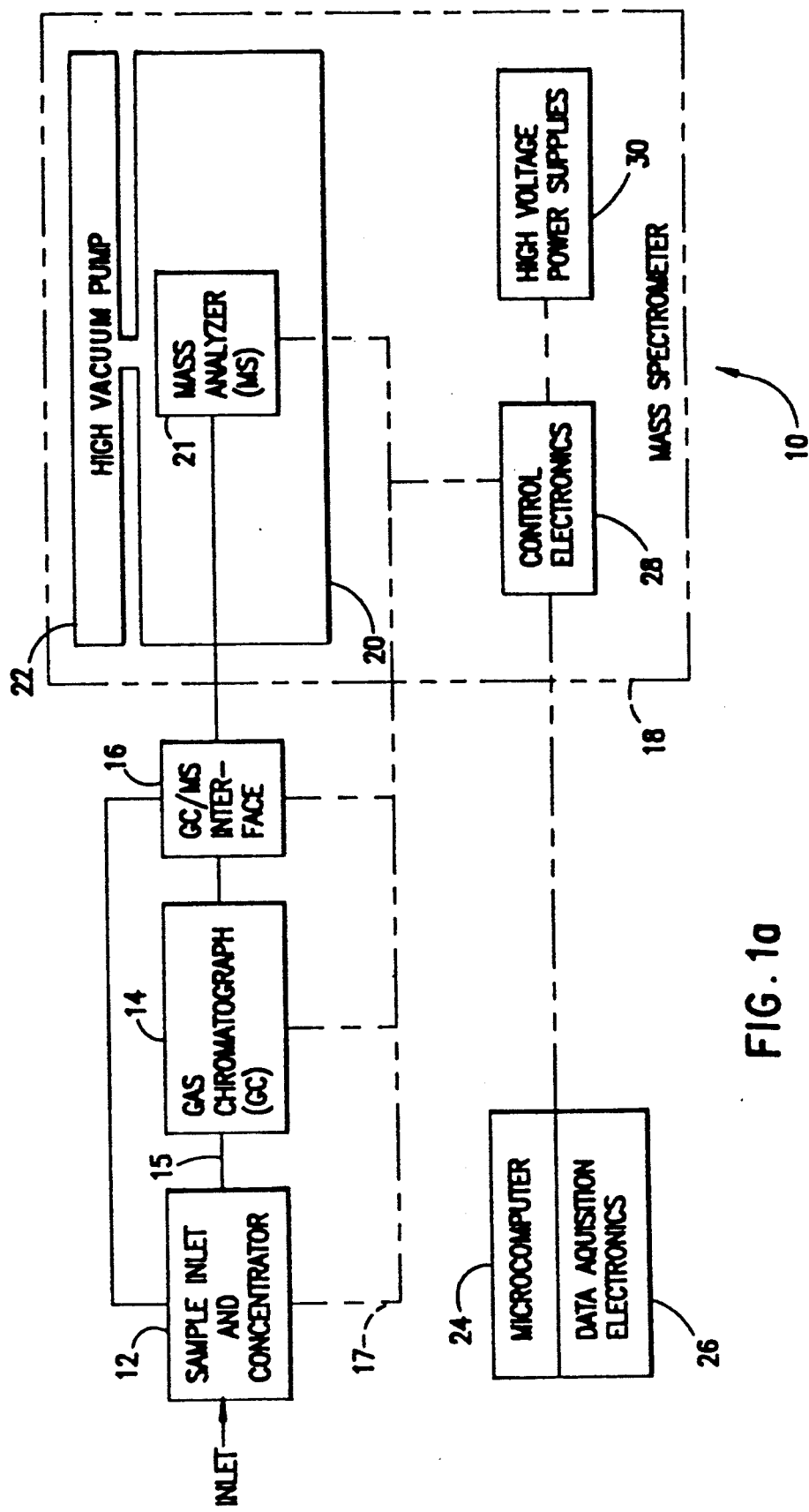
FIG. 1a is a block diagram showing the various major components of a preferred embodiment apparatus of the present invention.
Figure 2A:
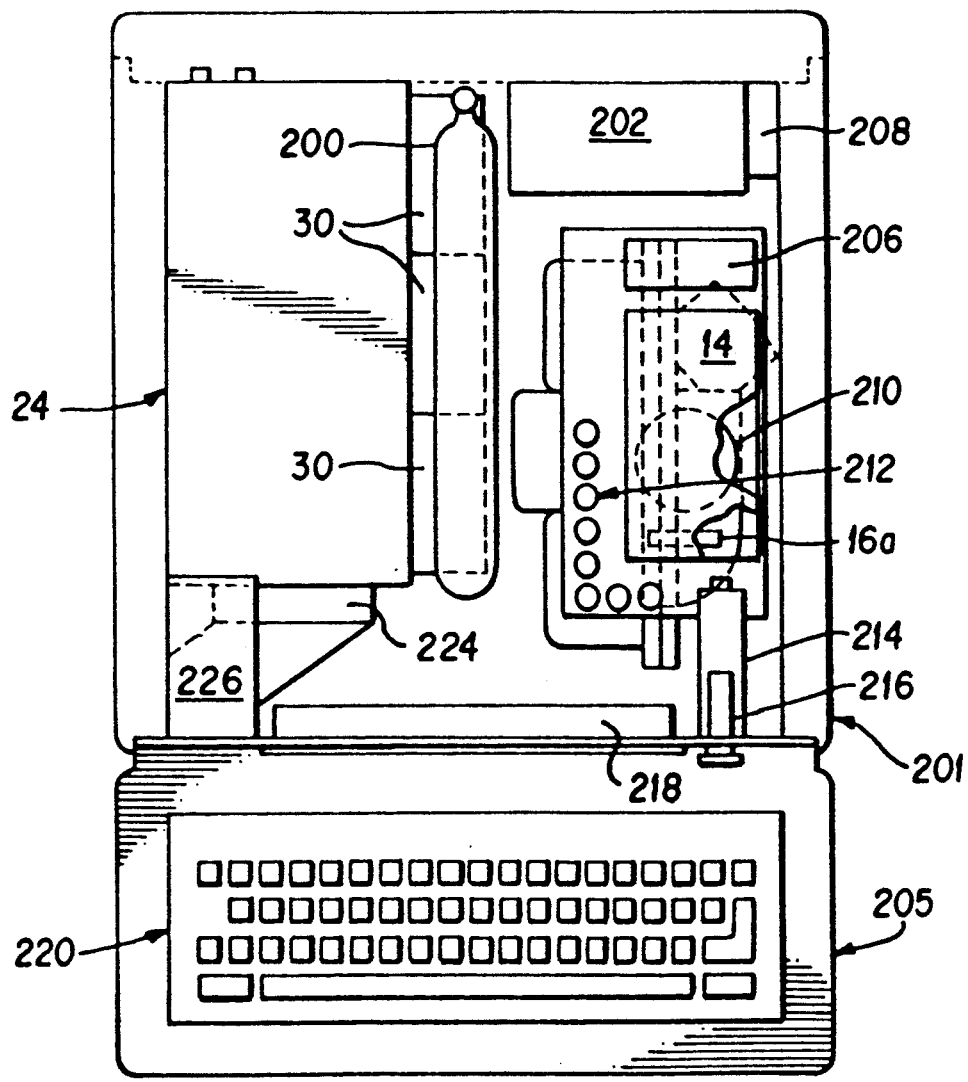
FIG. 2a is a drawing of a top view of the present miniaturized mass spectrometer system of the present invention mounted in its carrying case.
Figure 2B:
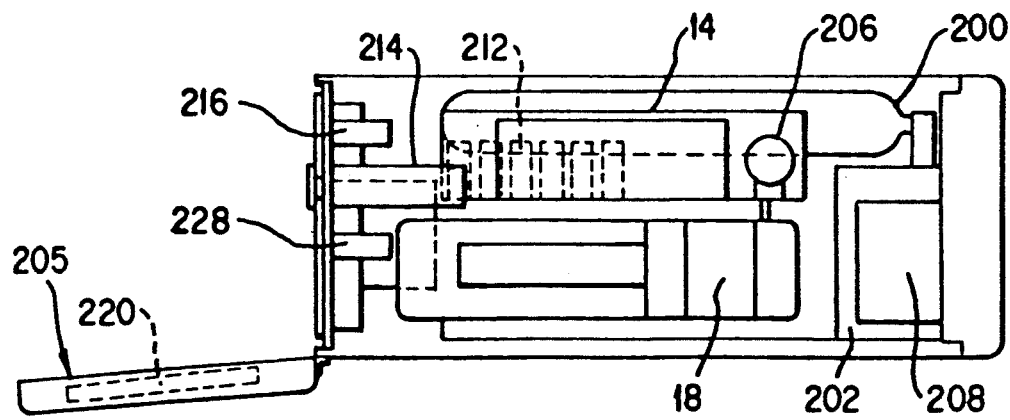
FIG. 2b is a drawing of a side view of the present miniaturized mass spectrometer system of the present invention mounted in its carrying case.
Figure 2C:
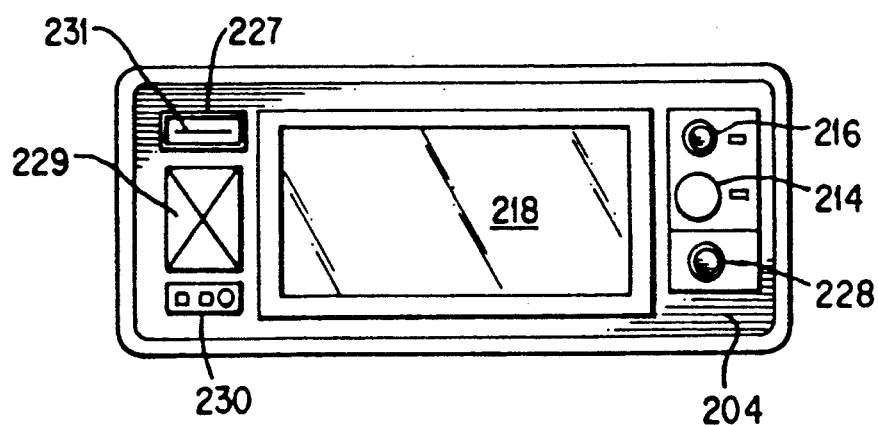
FIG. 2c is a drawing of a front view of the present miniaturized mass spectrometer system of the present invention mounted in its carrying case.

Referring now in detail to the drawings wherein like parts are designated by like reference numerals throughout, there is illustrated in FIG. 1a a schematic block diagram showing the preferred embodiment of the apparatus of the present invention. The preferred embodiment of the invention utilizes one or more magnetic sector mass analyzers, such as the Nier-Johnson ion optics with a 90° electrostatic analyzer and 90° magnetic analyzer. However, other types of known mass analyzers can be used such as quadrapoles and ion traps. FIGS. 2a-2c show additional details of the disclosed system.

Figure 14:
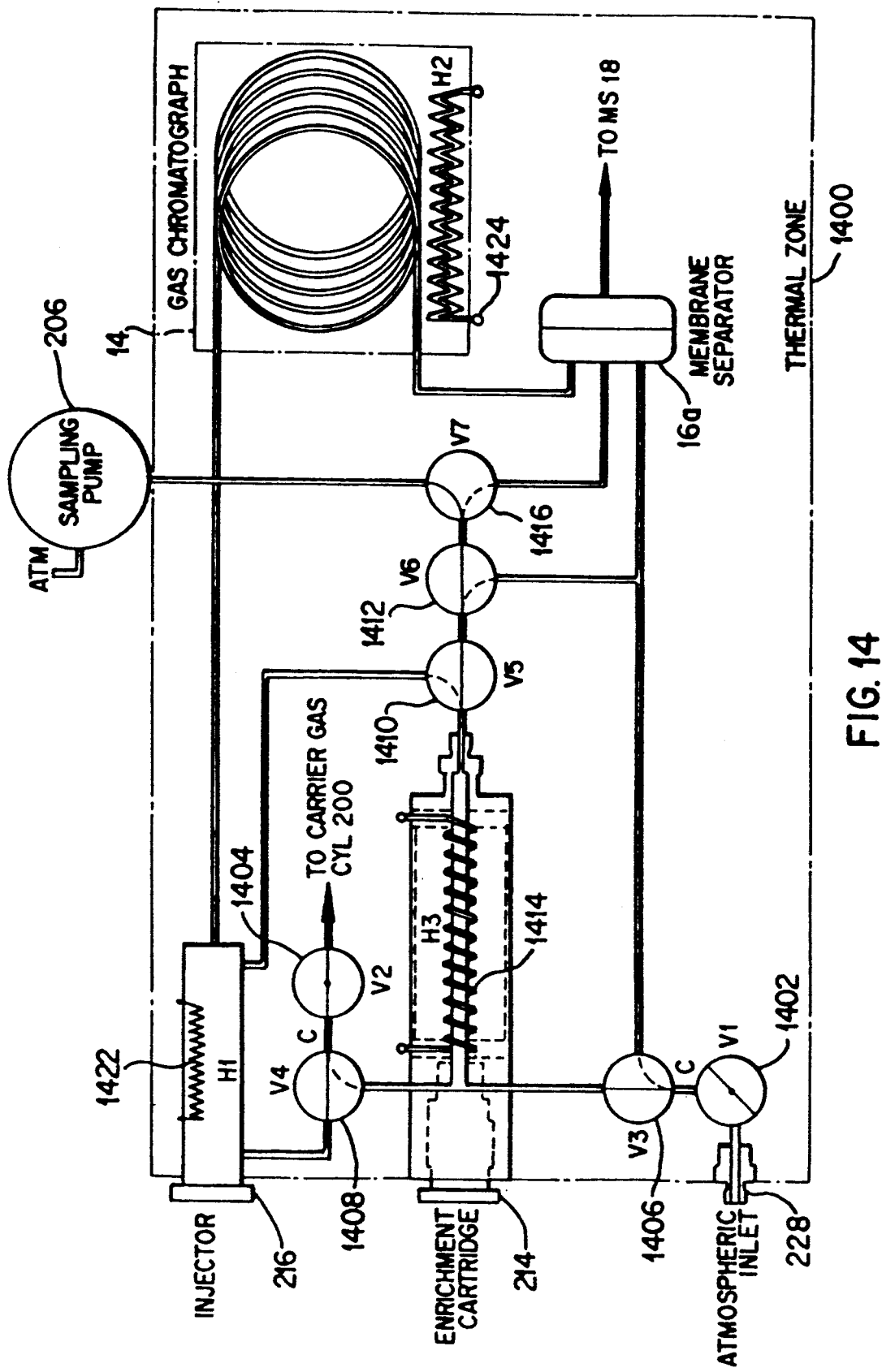
FIG. 14 is a schematic drawing of the sample flow and valving layout for use with the miniaturized mass spectrometer system of the present invention.

The miniaturized mass spectrometer system 10 of the present invention includes a sample inlet and concentrator assembly 12 which functions to gather the sample to be tested. The sample inlet and concentrator assembly consists of an atmospheric inlet 228, injector port 216, concentrator 214, gas chromatograph 210, sampling pump 206, valves 212, GC interface 16 and related tubing and fittings. The relationship between these elements and the sample flow through this assembly 12 is illustrated in FIG. 14.

The sample inlet and concentrator assembly 12 may consist of a port which is used for atmospheric or other sampling. The sampling by the atmospheric inlet may be accommodated using an on-board sampling pump 206 and a concentration cartridge loaded with an adsorbent, such as TENAX-C, which is thermally desorbed onto the gas chromatograph column 210 prior to the analysis run of the sample.

In addition to an atmospheric sampling mode, the present invention can be used in a direct injection sampling mode. This mode is similar to the method used for conventional laboratory gas chromatograph analysis, in which a sample is extracted into a solvent and a syringe is used to inject a calibrated amount of sample into the injection port 216 for the sample. The solvent is volatilized and carried through the gas chromatograph column by the carrier gas, in the same manner in which conventional gas chromatograph analyses are performed.

Both the injection port 216 and the atmospheric inlet port 228 are located on the front panel 204 of the miniaturized mass spectrometer system 10 of the present invention, as shown in FIGS. 2a-2c. In the event that a sampling probe is to be used, it is connected to the atmospheric inlet port 228. In that manner, the miniaturized mass spectrometer system 10 of the present invention is flexible in operation, with all of the necessary inlet connections being readily accessible to the operator.

The ability of the miniaturized mass spectrometer system 10 disclosed herein to perform both atmospheric analyses and analyses of samples in a solvent matrix allows the apparatus of the present invention to be used for a variety of analytical roles. For example, the instrument can be used to test water quality with samples taken from storage or other locations, prepared for analysis using simple solvent extraction cartridges or purge and trap devices or other suitable extraction methods and then induced into the instrument disclosed herein for identification of the unknown constituents of the sample.

In a similar fashion, solid samples can be analyzed, provided that they can be suitably prepared for injection. For these injection runs of the gas chromatograph, an additional sampling processing kit or devices is provided with the necessary solvents, mixing containers, extraction cartridges, measuring devices and simplified instructions such that the proper sample operation can be carried out by relatively minimally trained personnel. Such use of the present invention will be obvious to those of ordinary skill in the art. Thus, with proper sample preparation, the disclosed miniaturized mass spectrometer system 10 is capable of providing analysis of much more than simple atmospheric samples.

From the sample inlet and concentrator assembly 12, the sample is transferred into the gas chromatograph assembly 14. In order to provide for a miniaturized mass spectrometer system which can be used and is useful for a broad array of environmental sampling tasks, including the analysis of injected samples in a solvent matrix, a gas chromatograph column 210 having a performance that is consistent with the detailed analysis of unknown samples is preferably utilized as a part of the gas chromatograph assembly 14. The present invention utilizes a fused silica capillary tube, such as a 0.25 millimeter inner diameter column whose inside is coated with a polymer and is available as stock number DB624 from Supelco, Inc.

The gas chromatograph assembly 14 includes an oven which surrounds the gas chromatograph column 210. The oven is heated under control of the on-board computer system 24. A fan is used to ensure a high degree of uniformity of heat distribution within the oven. In addition, the temperature is controlled by using thermocouple sensors to read the internal temperature in the oven and a control loop to the oven heater to maintain the oven temperature on a pre-programmed temperature profile. Thermal fuses are provided in order to protect the system from accidental over-temperature heating caused by runaway heaters or controls.

The temperature of the oven and the heating rate are variable and can be set by the operator of the miniaturized mass spectrometer system 10 to ensure that an optimum analysis of the sample under test is accomplished. Valves 212 are provided for control of the carrier gas and the routing of the sample and other flows through the system. The valves 212 used with the system are designed to have a minimum reactivity with the sample material such that the maximum amount of sample reaches the gas chromatograph column 210. It is preferred that low reactivity glass-lined tubes and other low reactivity materials be utilized for that purpose. All of the valves 212 may be electrically controlled by latching solenoid mechanisms or other means, are power efficient and are suitable for gas chromatography.

The gas chromatograph assembly 14 is connected to the mass spectrometer system 18 by means of a gas chromatograph-mass spectrometer (GC/MS) interface 16. The GC/MS interface 16 serves to interface the gas chromatograph column 210 of the gas chromatograph assembly 14, which operates at a pressure of one atmosphere or slightly above and the mass analyzer 21 of the mass spectrometer assembly 18, which operates at about $10^{-4}$ to $10^{-6}$ Torr. of pressure. While several different types of interfaces can be used, for example, direct gas chromatograph coupling, a jet separator, a Watson-Biemann separator or a membrane separator, in the preferred embodiment, a membrane separator 16a is utilized. Membrane separators have advantages over the other types of separators because they are small in size, rugged and do not need a separate pumping system. In addition, the membrane separator of the present invention also provides a degree of sample enrichment and concentration and improves the signal-to-noise ratio over the carrier gas background by two or three orders of magnitude.

The membrane separator 16a functions to separate out the carrier gas by selectively passing the organic compounds into the mass analyzer 21 and thereby reducing the gas load that must be removed by the vacuum pump 22. This makes the use of an ion pump practical for portable low power operation.

The membrane material preferably used with the present membrane interface 16a is of dimethyl silicone, of one mil thickness. This material is available from the General Electric Company and remains stable at temperatures up to 200° Centigrade.

An alternative interface, a direct capillary gas chromatograph GC/MS interface 16, may be utilized in conjunction with a higher capacity external vacuum pump. Such an alternative interface provides a more sensitive and accurate quantization of the relative composition of the sample.

The concentrated sample is routed from the GC/MS interface 16 to the input of the mass spectrometer system 18. As will be described more fully herein, the mass spectrometer system 18 utilizes a magnetic field of about 7.5–15K gauss and a commercially available ion detector 44 to obtain a sufficient gain from the detector, preferably of $10^4$–$10^6$ or better. The ion source 34, which will also be discussed later herein, is preferably partly constructed from a machinable ceramic material, such as Macor, available from Corning. The mass analyzers 21 and 23 (FIG. 1b) of the mass spectrometer system 18 and some internal parts may preferably be constructed from stainless steel and all interior surfaces that might be exposed to ions should be gold-plated.

In the preferred embodiment, the mass analyzer assembly 21 includes an ion source 34, an electric sector 36, magnetic sector 40, ion detector 44 and precision alignment device 500, all of which are enclosed within a vacuum envelope 20 which may be constructed from any number of materials, such as aluminum, stainless steel, engineered plastics, or ceramic materials. A vacuum pump 22 is either enclosed within or connected to the vacuum envelope 20 in order to maintain a vacuum of $10^{-4}$ to $10^{-7}$ Torr. A high vacuum valve 46 is provided for rough pumping when using an internal ion vacuum pump 42 or between an external vacuum pump 22 and the mass analyzer 21.

Figure 15:
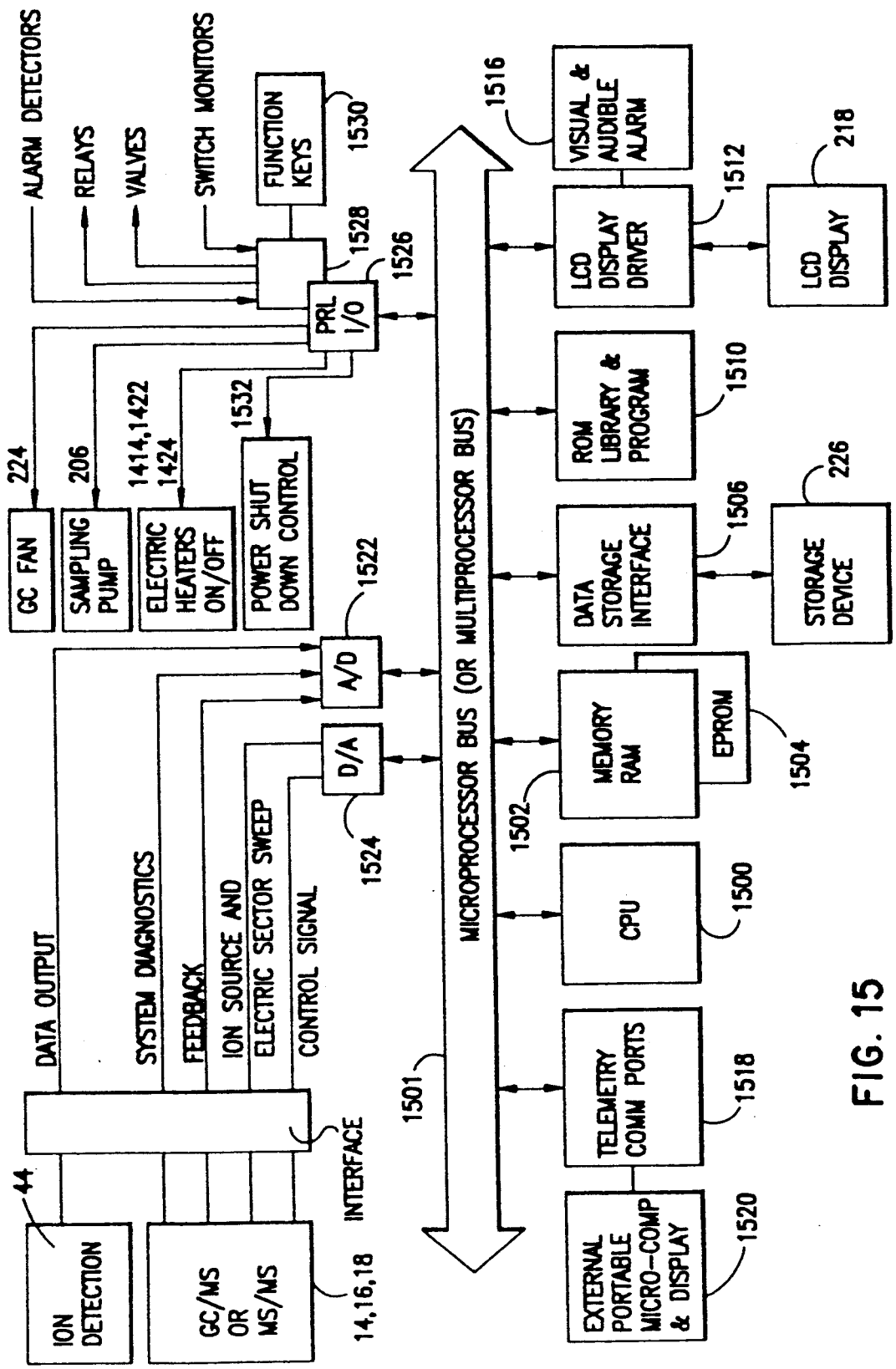
FIG. 15 is a schematic diagram showing the operation of the computer and control system used with the present invention.
Figure 16:
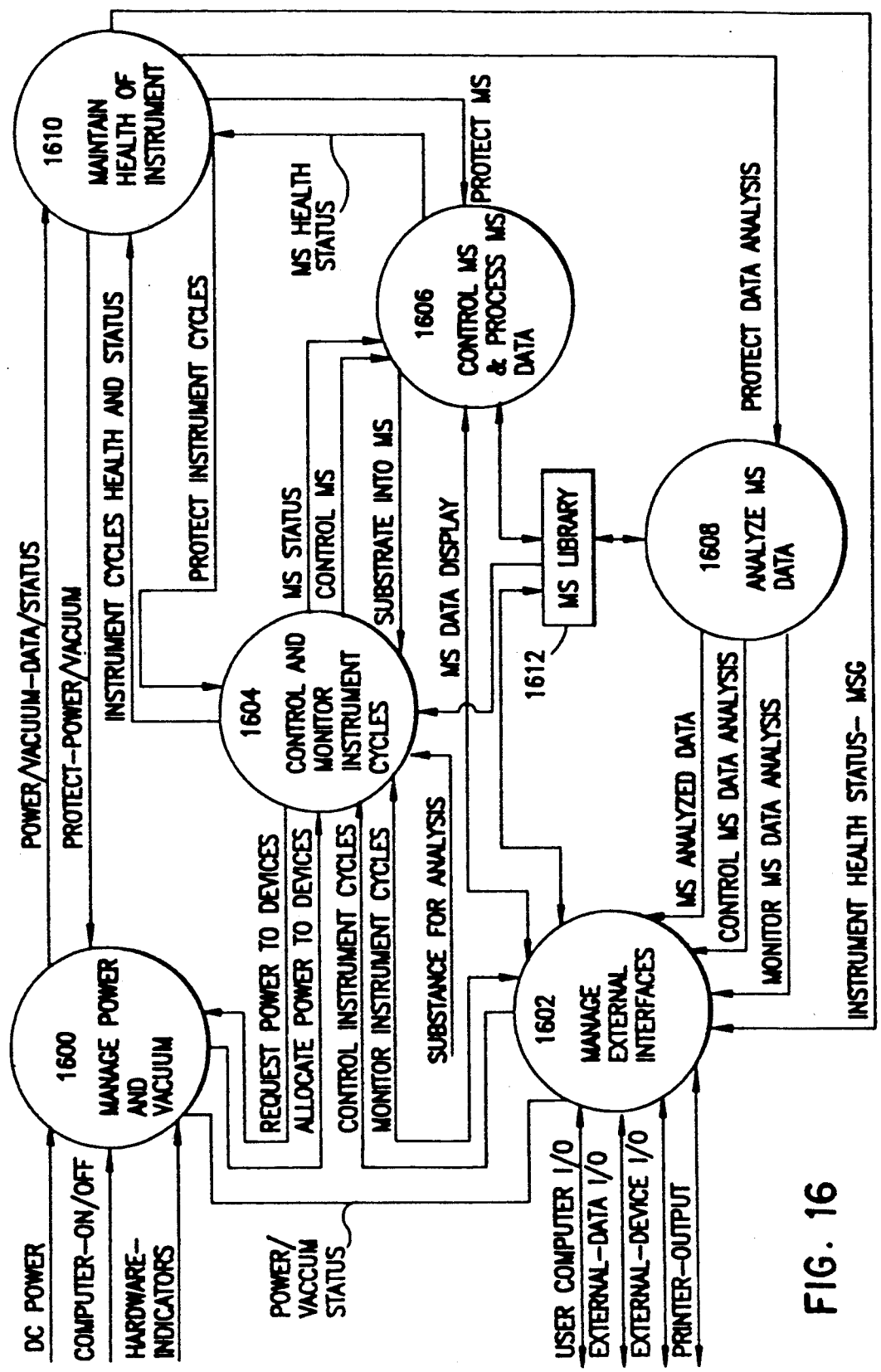
FIG. 16 is a flow chart showing the functions performed by the software which operates the miniaturized mass spectrometer system of the present invention.

The miniaturized mass spectrometer system 10 of the present invention is controlled by an on-board microcomputer 24, data acquisition 26, and control electronics 28. The microcomputer may preferably be an IBM compatible AT or PS/2 class microcomputer, with a real-time multi-tasking operating system. The microcomputer 24, data acquisition 26, and control electronics module 28 includes a display 218, keyboard 220, and other components, which are shown and discussed in connection with FIGS. 2a-2c. A flow chart showing the operation of the computer and control systems which operate the miniaturized mass spectrometer system 10 is shown in FIG. 15. A flow chart showing the functions of the software is shown in FIG. 16. Data acquisition electronics 26 as well as high voltage power supplies 30 for the mass analyzer 21 components (ion source 34, electric sector 36 and ion pump 42), are also provided.

The control electronics 28, microcomputer 24, data acquisition electronics 26 and high voltage power supplies 30 may be powered by portable batteries 202 such that the miniaturized mass spectrometer system 10 of the present invention can be a truly portable and self-contained system. Preferably, a sealed, lead-acid battery may be utilized. Alternatively, batteries constructed from lithium or other exotic materials, but at much greater cost, may also be utilized.

Alternatively, a small gasoline powered electric generator or external battery pack or fuel cells could be used to provide power, particularly if an external high vacuum system 22 is utilized.

The main I/O interfaces between the computer 24 and the various electrically operated elements of the system are shown in FIG. 15. The microcomputer system 24 may be utilized to display the analytical results of the analysis as well as to provide a display of the control diagnostic information, for example, the carrier gas supply and vacuum levels, by displaying such values through, for example, a flat plate display 218. The microcomputer 24 preferably includes a removable solid state memory card of preferably at least 1 Mb capacity for use in a removable solid state memory card drive 226. Alternatively, a floppy disk drive or hard disk drive may be utilized. In that manner, the operational program for the miniaturized mass spectrometer system 10 may be stored on-board the system. It can also store an on-board mass spectra library for identifying the analyzed samples and provide a means for recording the results.

Figure 1B:
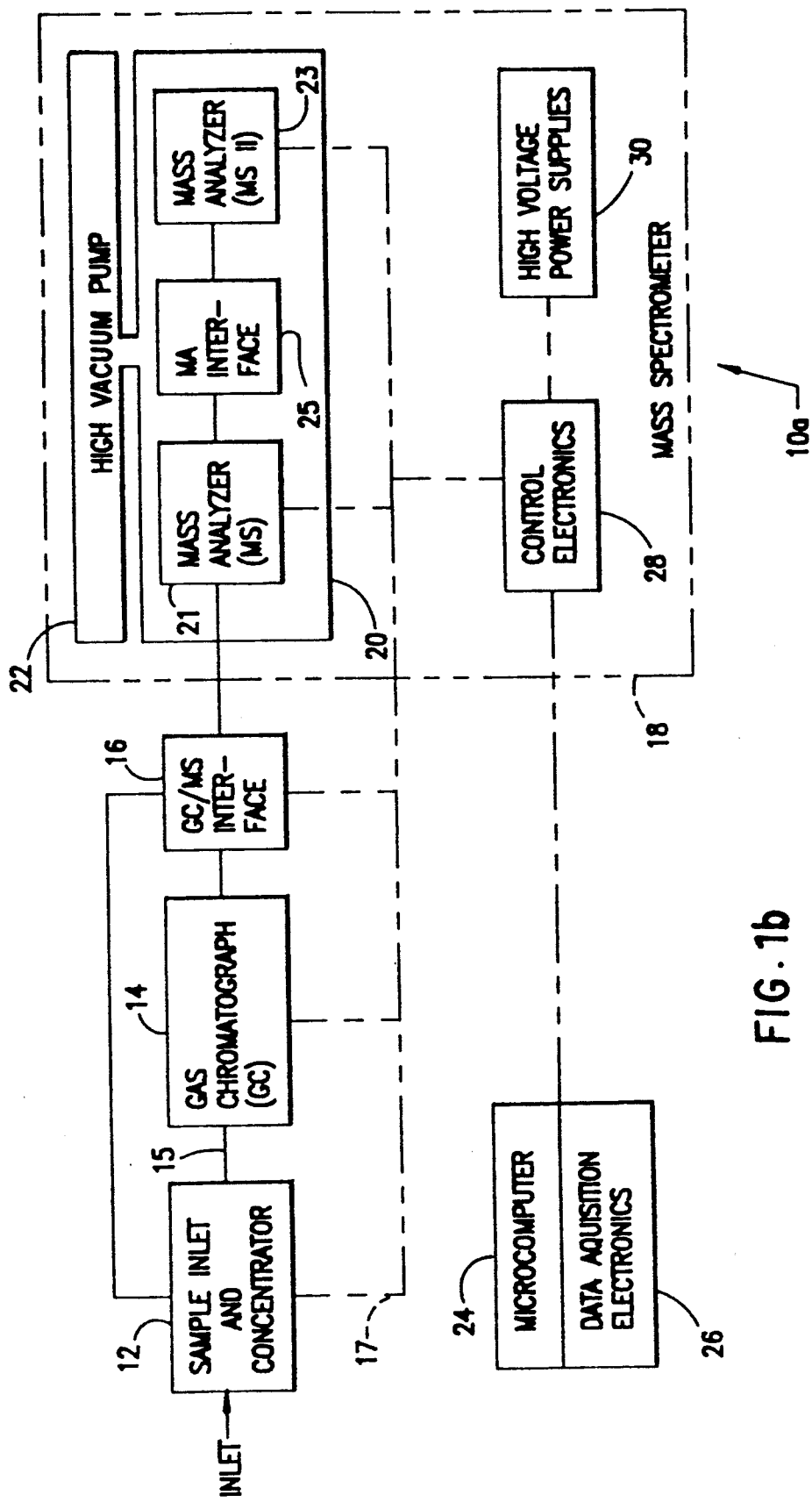
FIG. 1b is a block diagram showing the various major components of an alternate tandem mass analyzer embodiment of the apparatus of the present invention.

In both FIGS. 1a and 1b, the solid lines 15 interconnecting the elements represent the sample gas flow between those elements. The dotted lines 17 represent the electronic or electrical control lines.

FIG. 1b shows an alternate embodiment of the mass spectrometer system 18 in which two mass analyzers 21 and 23 are utilized in place of the single mass analyzer 21 of FIG. 1a. In the alternative tandem MS embodiment, the first mass analyzer 21 contains the ion source 34, electric sector 36, and magnetic sector. The second mass analyzer 23, contains another electric and magnetic sector and the ion detector 44. In such a tandem mass spectrometer, the two mass analyzers 21 and 23 are interconnected by means of a mass analyzer interface 25. Such a system provides for greater sensitivity and resolution than the single mass analyzer mass spectrometer 18 of FIG. 1a. The mass analyzer interface 25 provides secondary ionization of the sample gas by means of surface induced ionization (SID). The preferred method of SID is to use a multi-channel plate or other similar means to produce multiple ion collisions through parallel channels. This SID method provides a high degree of ionization efficiency without requiring additional vacuum pumping otherwise required by conventional chemical ionization methods.

FIGS. 2a-2c show respectively top, side and front views of the instant miniaturized mass spectrometer system 10 mounted in a single enclosure or case preferably having the dimensions of 20 inches in width by 20 inches in length by 10 inches or less in height. Such a system, which preferably weighs less than 75 pounds, can readily be carried by the operator from place to place and is a truly portable analytical grade miniaturized mass spectrometer system. The layout of the major components of such a system is shown in FIGS. 2a-2c.

Referring now to FIG. 2a, there is shown the placement of the microcomputer 24, which includes a card cage for carrying various interface cards, as well as its own power supply, random access memory (RAM) and other on-board memory (EPROM, SRAM, ROM), as is well known in the art. A carrier gas bottle 200 is shown mounted in the case 201, whose function will be described hereinafter. A battery pack 202 is provided, as has been previously described.

Alternatively, in the event that an external high vacuum pump is utilized, as has also been previously described, the battery pack 202 may not be practical to use to operate the instant miniaturized mass spectrometer system 18 and thus the high vacuum external (to the vacuum envelope 20) pump 22 is located where the batteries 202 would otherwise be situated. A DC/AC filter and converter 208 is also utilized and is located next to the battery pack 202. The DC/AC filter and converter 208 serves to reduce power line fluctuations such that they are prevented from being passed into the mass spectrometer system 10.

A sampling pump 206, whose function will be described later, is also contained within the case 201. Adjacent to the sampling pump 206 is the gas chromatograph assembly 14, which includes the oven and other heating controls and elements (used for heating the gas chromatograph column 210 itself). A membrane separator 16a is located adjacent to and is connected to the output of the gas chromatograph column 210, in a known manner. An array of electronically or electrically controlled valves 212, (including 1402, 1404, 1406, 1408, 1410, 1412 and 1416 as will be described later herein), are located adjacent to the gas chromatograph assembly 14 and above the mass spectrometer system 18. A fan 224 is provided to cool the components located inside of the case 201 through an opening 229 in the front face 204. A plurality of high voltage power supplies 30 are provided below the carrier gas bottle 200.

As has been previously described, a removable solid state memory card drive 226 is provided within the enclosure 201 and is located such that the front face 227, which includes an access slot 231 is accessible to the operator through the front panel 204 of the case 201 Also accessible from the front face 204, as shown in FIG. 2c, is the atmospheric inlet port 228, the injector port 216 and the thermal desorb cartridge assembly 214. The front face 204 of the case also includes a power and indicator light panel 230, having LEDs for indicating the power on, vacuum on and ready condition of the miniaturized mass spectrometer system 10. In addition, an LCD display 218 or other type of flat panel display is also included in the front panel 204 for use by the operator of the present system. A standard computer type keyboard 220 is provided as part of a hinged front cover 205 such that the operator can communicate with and control the instant miniaturized mass spectrometer system 10, as will be described later herein.

Figure 3A:
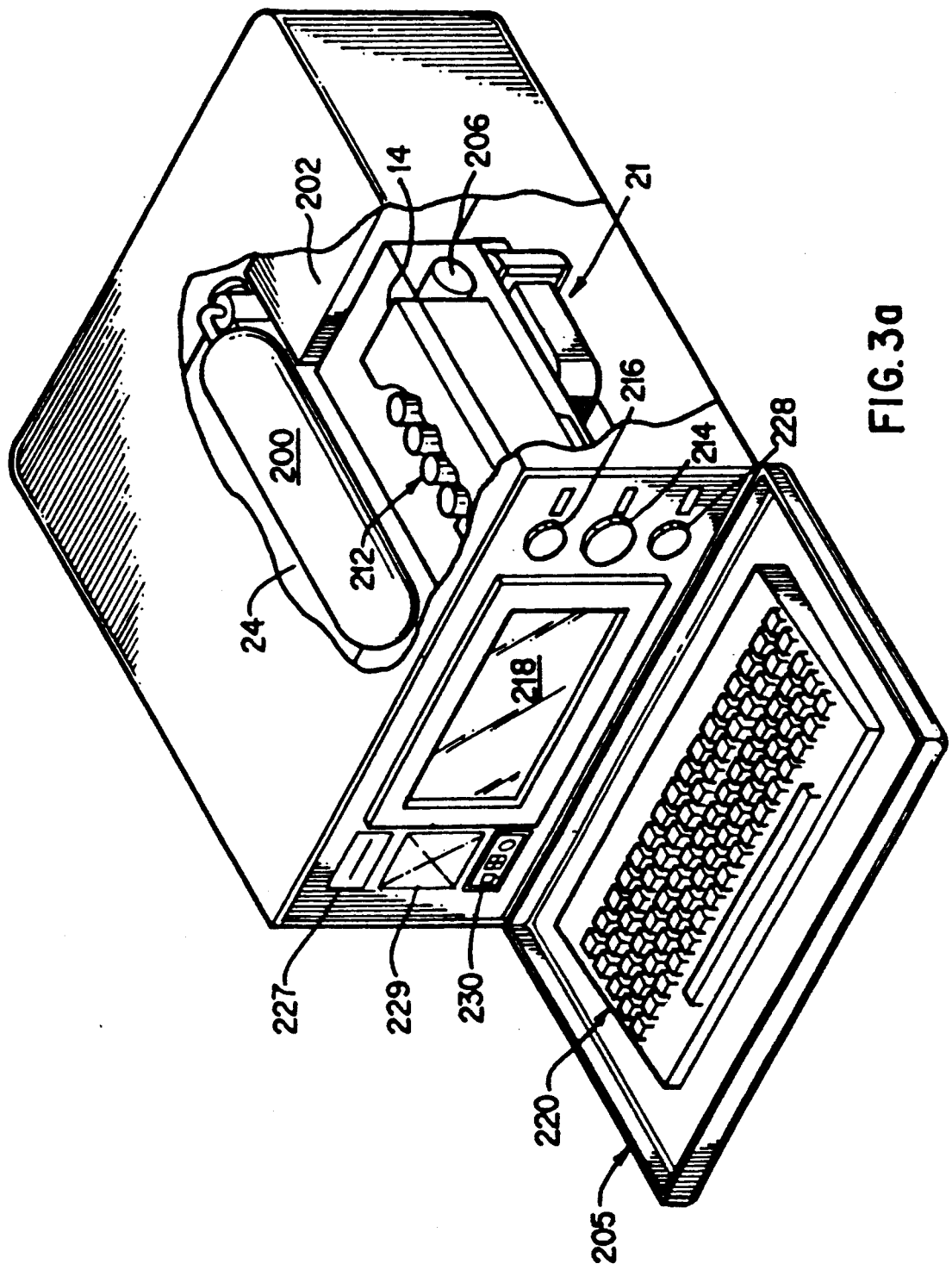
FIG. 3a is an isometric drawing of the mass spectrometer system of the present invention showing the placement of the major components and assemblies including a gas chromatograph and front panel in its carrying case.

FIG. 3a shows a complete view of the present miniaturized mass spectrometer system 10 of the present invention including the location of the gas chromatograph and the front panel with displays and inlet ports.

Figure 3B:
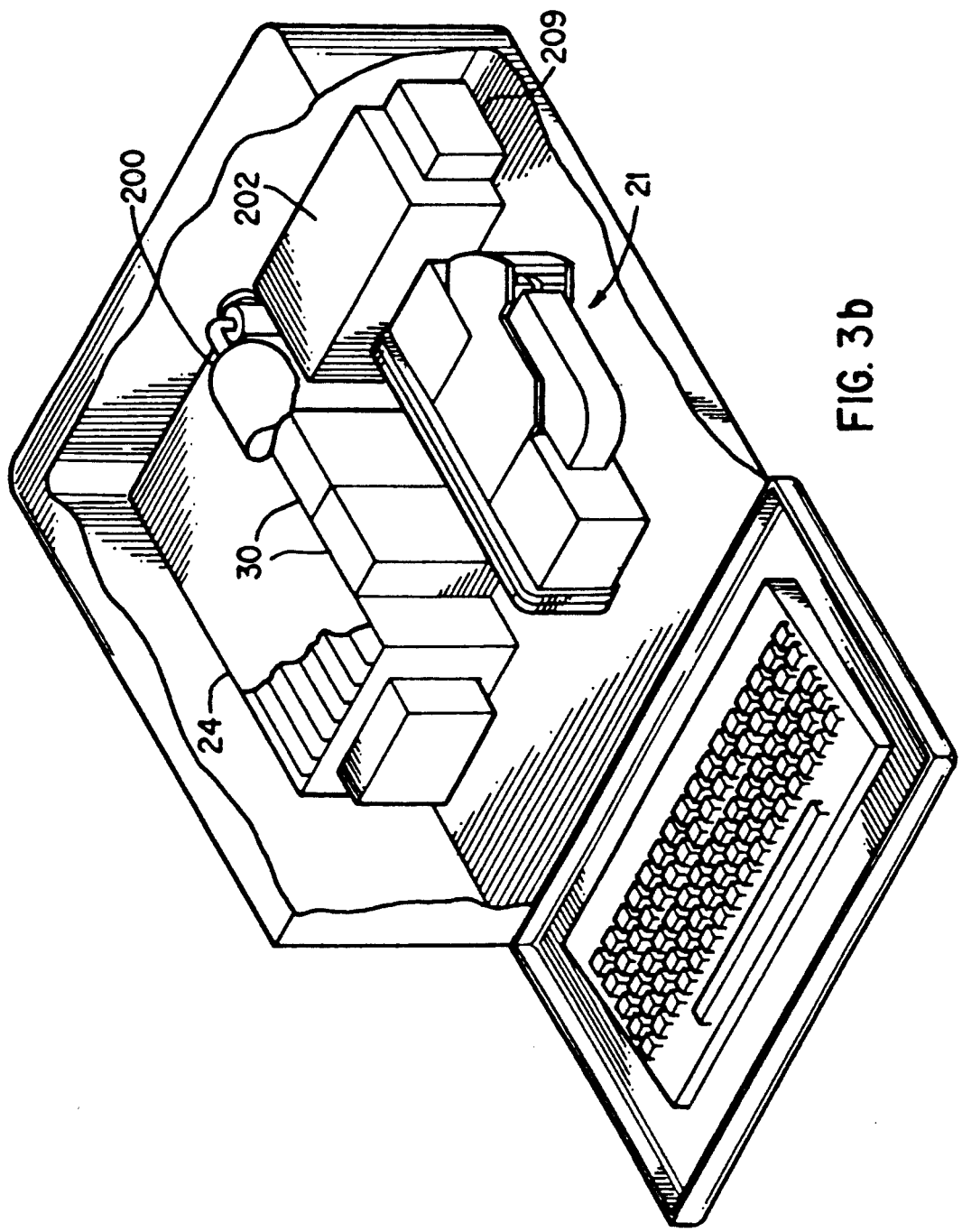
FIG. 3b is an isometric drawing showing the placement of major components and assemblies of the mass spectrometer system of the present invention with the GC removed for clarity of view of the mass analyzer and other key components.

FIG. 3b shows an isometric diagram of the preferred embodiment of the mass spectrometer system 10 of the present invention described above, but with the gas chromatograph removed and a cutaway view of the carrier gas cylinder 200 to clearly show the placement of other major components.

Figure 4A:
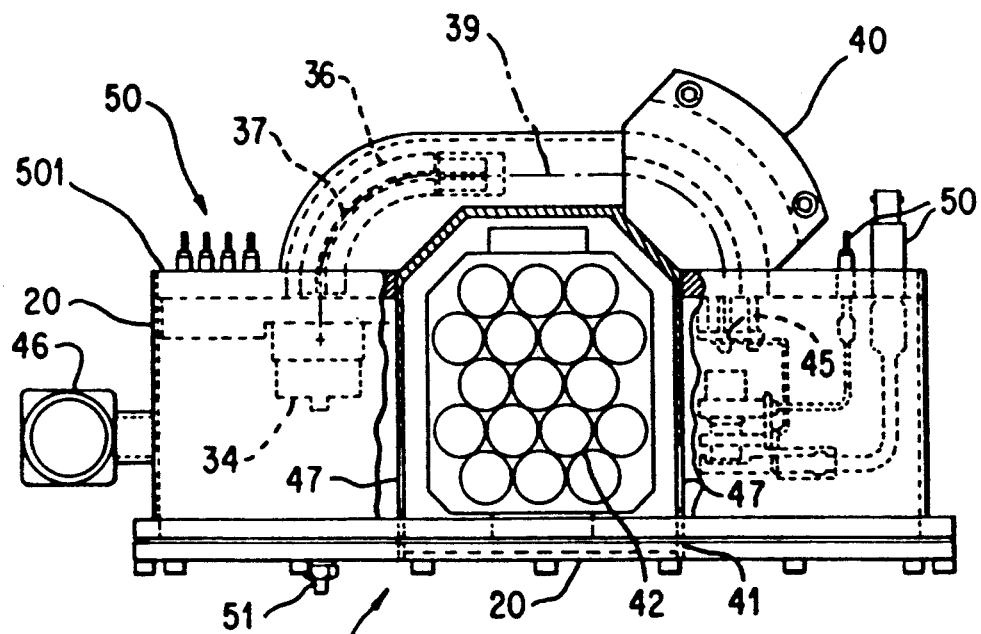
FIG. 4a is a cross-sectional drawing of the top view of the preferred embodiment of the mass analyzer assembly including the precision alignment housing and magnet assembly used with the present invention.
Figure 4B:
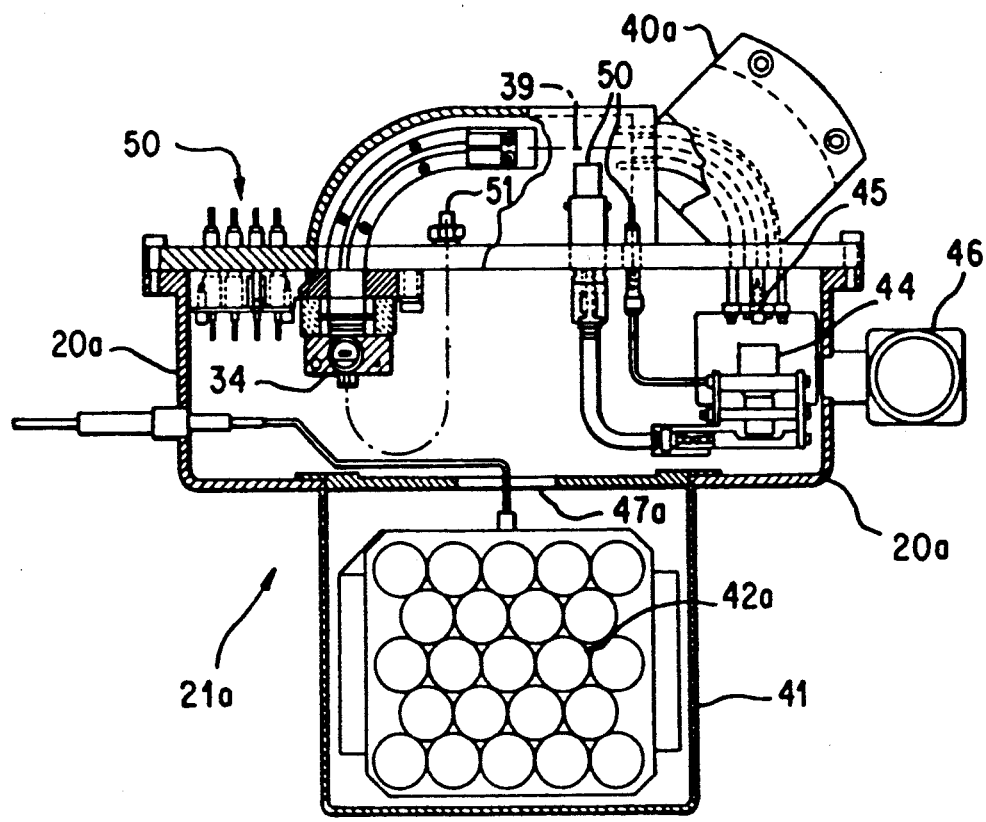
FIG. 4b is a cross-sectional drawing of the top view of an alternate embodiment of the mass analyzer assembly including a precision alignment housing, magnetic assembly, and separate ion pump magnet used with the present invention.

FIGS. 4a and 4b show the general layout of the components which comprise the mass analyzer assembly 21 which forms a part of the mass spectrometer system 18 of the present invention. In the preferred embodiment of the mass analyzer 21 shown in FIG. 4a, the integral ion pump 42 is adjacent to the magnetic analyzer 40 to provide the maximum ion pumping volume in the most compact vacuum housing 20 possible.

In the alternate embodiment of the mass analyzer 21a shown in FIG. 4b, the integral ion pump 42a is located at the front of but within the same vacuum envelope 20a. The magnetic analyzer 40 and ion pump 42 appendage magnets share a common yoke structure as explained elsewhere. In an alternative embodiment, the magnetic analyzer 40a and ion pump appendage magnets have separate yoke structures. The ion pump 42, 42a is surrounded on all sides by a magnetic yoke 41, 41a which may be built into the vacuum housing 20, 20a. The mass analyzer components located within the vacuum housing 20, 20a must be operated in a high vacuum. Thus, the electric lines needed to power and control these components must be brought through vacuum-tight electrically insulated connectors called feedthroughs 50.

As shown in FIGS. 4a and 4b, the sample from the gas chromatograph system 14 is input from the membrane separator 16a into the vacuum housing 20, 20a and into the ion source 34 as a vapor at low pressure. A vacuum-tight Swagelock fitting 51 is provided to connect the sample line from the membrane separator 16a for this purpose. Electrons produced by the filament contained within the ion source 34 bombard the sample molecules at an energy of about 70 eV, creating positive ions. Such a process is generally referred to as electron impact ionization. The positive ions which result are accelerated out of the ion source 34, forming an ion beam in a known manner and then into the electric sector 36.

The ion source 34 is connected to one end of an electric sector 36 through use of an electric field shunt which reduces fringing field effects. Certain ionized particles of the sample travel through an electric field 37 established by the two parallel plates of the electric sector 36. The electric sector 36, which functions as an electrostatic analyzer, produces a radial electric field 37 which deflects the ions produced by the ion source 34. The deflection produced in the electric sector 36 is proportional to the energy of the ions. Thus, ions having slightly different energies when they enter are selectively filtered out so that the ions emerge from the electric sector 36 with highly defined energies. The ions exit the electric sector 36 and are directed to the magnetic analyzer, which is formed by the permanent magnet assembly 40.

The magnetic analyzer separates the ions according to their relative mass-to-charge ratios. An integral ion pump 42 is used to ensure that the mass analyzer system is maintained at a high vacuum. Alternatively, a high vacuum pump 22 may be connected externally to the vacuum envelope 20, 20a to provide the required high vacuum conditions.

Since the trajectory of an ion in the magnetic field of the permanent magnet assembly 40 is proportional to its momentum, by altering the accelerating voltage of the ion source 34, an ion of a chosen mass can be directed through an exit slit 45 to the ion detector 44.

Because the ions passing through the field of the permanent magnet assembly 40 are deflected according to their momentum, ions of the same mass but slightly different velocities (a function of energy) will follow different paths. Thus, without the electric sector or electrostatic analyzer 36, the image width produced by the magnet assembly 40 would be greater, and the resolution greatly reduced.

After the ions pass through the field of the permanent magnet assembly 40 and the exit slit 45, they enter the ion detector 44. The ion detector 44 is used to measure the relative intensity of the ion current. This information is converted from an analog signal to a digital signal and then passed to the data acquisition electronics 26 and microcomputer 24 and for processing.

The ion detector 44 utilized by the system of the present invention provides a fast response time with high sensitivity. One such type of ion detector that may be utilized is known as an electron multiplier. An electron multiplier consists of dynodes made of a certain material, for example, copper beryllium alloy, which has the property of emitting secondary electrons when bombarded with charged particles. In that manner, an amplification of more than $10^6$ can be achieved by a cascade effect of electrons producing more electrons from the initial impact. It is preferred that the ion detector 44 for use in the present invention be a continuous dynode electron multiplier. The signal from the ion detector 44 is amplified and fed to an analog-to-digital converter 1522 shown in FIG. 15 where it is digitized and then sent to the microprocessor control system 1500.

In order to provide the correct environment in which the processes described above can occur, the mass analyzer assembly 21 must be maintained under a vacuum. The mass analyzer assembly 21 of the present invention is pumped-out through a high vacuum shut-off valve 46 to a pressure of $10^{-6}$ to $10^{-7}$ Torr. to increase the mean free path of the ions and the probability that the ions will travel to the detector 44 without colliding with residual gas molecules. At a pressure of $10^{-7}$ Torr., the average distance an ion travels between collisions is long compared to the path length through the mass analyzer assembly 21.

A vacuum of this order may be produced by many different types of vacuum pumps, such as diffusion pumps which use jets of oil vapor to sweep molecules out of the high vacuum chamber, or turbomolecular pumps, which remove molecules by mechanical means. It is preferred that the present mass spectrometer system 18 utilize an ion pump 42, using a suitable custom designed or commercially available ion pump core. After the initial pump-out and bake-out of the mass analyzer assembly at an elevated temperature above 200° C. to remove the most significant out-gassing contaminants, the ion vacuum pump 42 is used to maintain the vacuum at the desired operational levels. The alternative is to use an external high vacuum pump, such as a turbomolecular vacuum pump or molecular drag pump with appropriate roughing pump for use with the alternate capillary direct GC/MS interface 16.

FIGS. 5a-5d show respectively the top and front views of a preferred embodiment of a precision alignment assembly 500 and a top and front view of an alternate embodiment of a precision alignment assembly 500a utilized with the present invention. The precision alignment assembly 500 provides a precise means of locating the major components of the mass analyzer assembly to each other such that the ion beam 39 is precisely aligned. In addition, the precision alignment assembly 500 provides a means of securing the aligned major components of the mass analyzer assembly 21 to the vacuum enclosure 20 in such a manner that the magnetic analyzer section 40 is readily aligned with the ion source 34, electric sector 36, exit slit 45 and detector 44 when mounted to the precision alignment assembly 500.

Figure 5A:
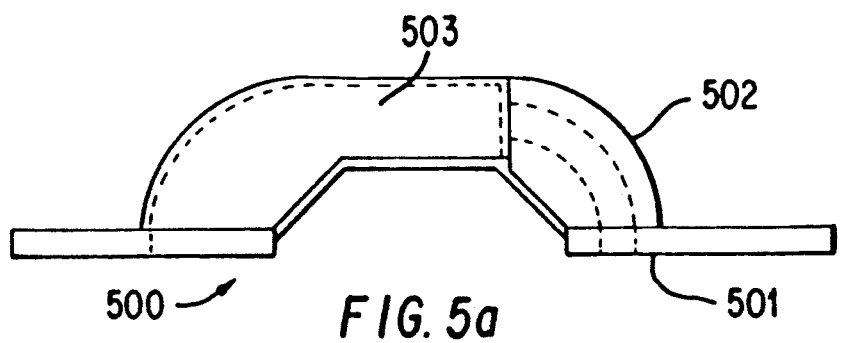
FIG. 5a is a drawing of the top view of the preferred embodiment of the precision alignment assembly used with the present invention.
Figure 5B:
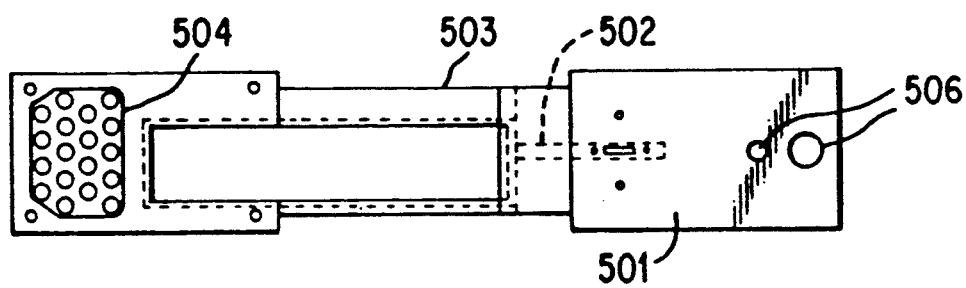
FIG. 5b is a drawing of the front view of the preferred embodiment of the precision alignment assembly used with the present invention.

As shown in FIGS. 5a and 5b, and as will be later described in connection with FIGS. 6a and 6b, which correspond to the precision alignment assembly 500 illustrated in FIGS. 5a and 5b, the precision alignment assembly 500 is formed by a precision alignment plate 501 and precision flight tube 503 which may be formed by casting, molding or welding into a single piece and then precision machined to provide the reference points required to align the active components of the mass analyzer 21 generating the ion beam. The precision alignment plate 500 provides a single device with various reference points to which to mount and align two or more of the components that create and control the ion beam within a three dimensional space or planes. The precision flight tube 503 is attached to the precision alignment plate 501 to enclose the electric sector and the narrow magnetic analyzer portion of the flight tube 502 between the analyzer magnets 40 within the vacuum envelope 20. Alternatively, the analyzer magnets may be enclosed within the flight tube 503.

Figure 6B:
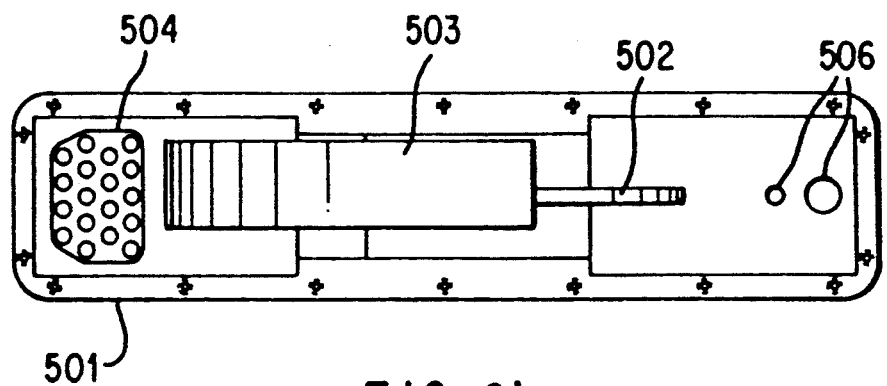
FIG. 6b is a drawing of the back view of the preferred embodiment of the precision alignment vacuum housing for use with the present invention.
Figure 6A:
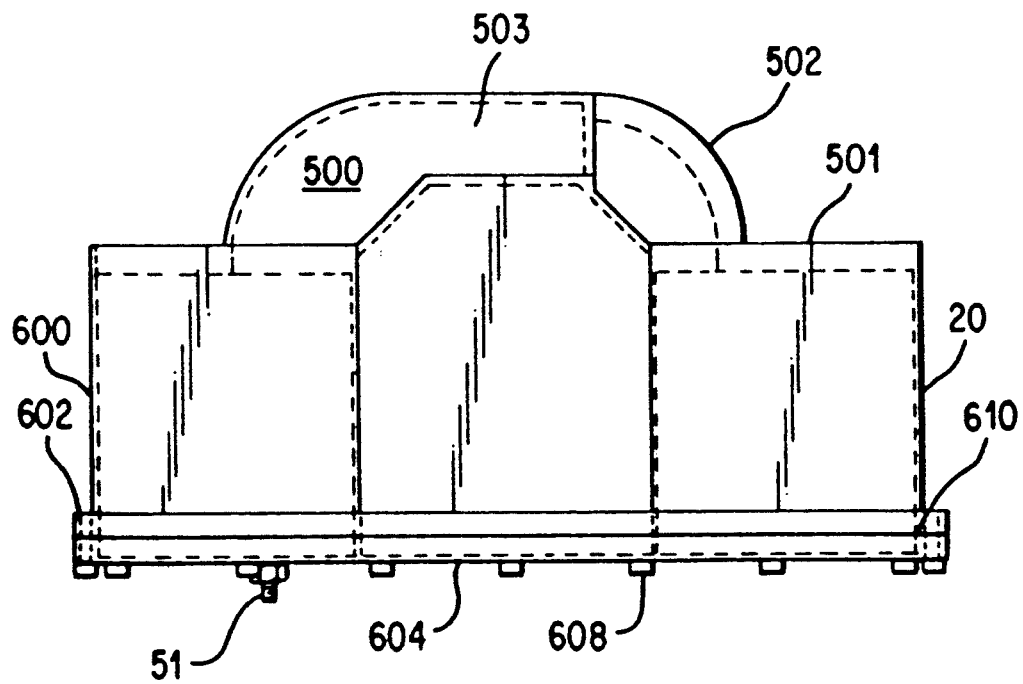
FIG. 6a is a drawing of the top view of the preferred embodiment of the precision alignment vacuum housing for use with the present invention.

In the preferred embodiment, the precision alignment assembly 501 forms a semi-U-shaped member as shown in FIG. 5a, which provides more space for the ion pump 42 adjacent to the analyzer magnet 40, and is welded, molded, or cast to form a part of the vacuum housing 20 as shown in FIGS. 4a and 6a. The precision alignment plate 501 also provides a flat surface for mounting insulated high vacuum feedthroughs 50 to pass the required electric lines through the vacuum housing into the mass analyzer. A sample line feedthrough 505 is also provided to pass the gas sample form the GC interface 16 into the mass analyzer 21 connected with a Swagelock fitting 51.

Figure 5C:
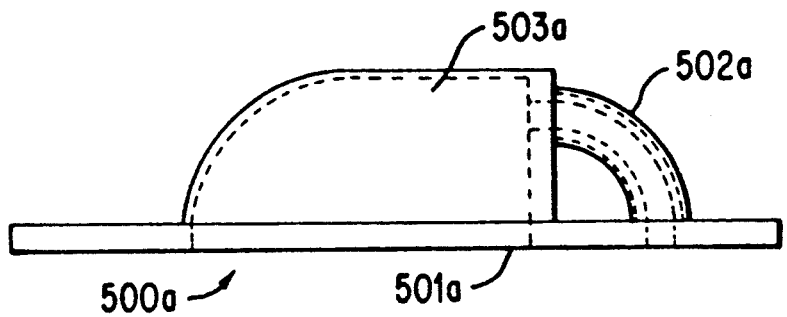
FIG. 5c is a drawing of the top view of an alternate embodiment of the precision alignment assembly used with the present invention.
Figure 5D:
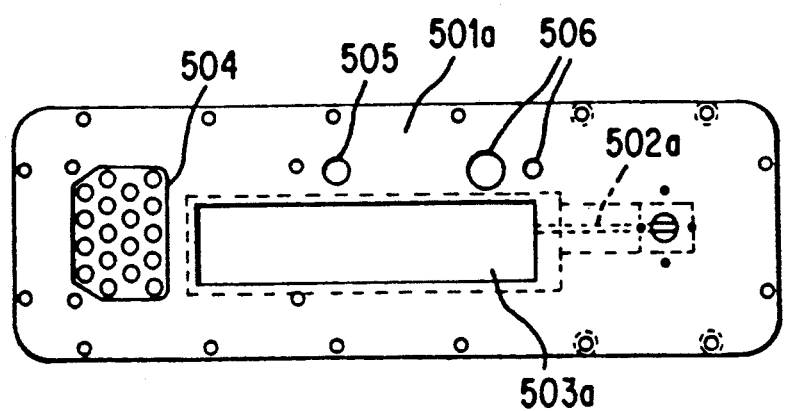
FIG. 5d is a drawing of the front view of an alternate embodiment of the precision alignment assembly used with the present invention.

An alternate embodiment of the precision alignment assembly 500a shown in FIGS. 5c and 5d includes a straight element 501a which functions in the same manner as the semi-U-shaped element 501 of FIGS. 5a and 5b. However, since the precision alignment assembly shown in FIGS. 5c and 5d is designed for use with the alternate embodiment of the mass analyzer shown in FIG. 4b, it serves an additional function as a vacuum flange to hold the high vacuum seal 610 as shown in FIG. 6c. The integral ion pump 42a is located on the other side of the vacuum flange 604a. A plurality of electrical feedthroughs 50 may be fixed to a feedthrough plate 504 to facilitate installation in the precision alignment plate 501, 501a in a way that is vacuum leakproof. Similarly, individual vacuum feedthroughs 50 may otherwise be welded or attached directly to the precision alignment plate through orifices 506 provided for this purpose.

FIGS. 6a and 6b show respectively the top and side views of a precision alignment vacuum housing for use with the preferred embodiment of the mass analyzer system 21 of the present invention. This vacuum housing, as has been described, includes elements formed as a part thereof which serve to align the components of the mass analyzer system 21 when they are mounted to the precision alignment assembly 500 which forms a part of the vacuum housing 20.

The vacuum housing 20 is comprised of the precision alignment assembly 500, the vacuum housing side walls 600, and a pair of vacuum flanges 602 and 604. These components are welded, cast or molded into a single vacuum-tight enclosure except for one of the vacuum flanges 604 which may be removed to provide access to the mass analyzer 21 components within. The vacuum flange 604 is removably secured to the housing flange 602 by means of a plurality of cap bolts 608. An O-ring or metallic wire seal 610 is utilized to form an essentially air tight seal between the vacuum flanges 602 and 604.

In the preferred embodiment, the vacuum housing 20 is of dimensions of approximately 3.5 inches in height, 10 inches in width and 6 inches in depth.

FIG. 6b is a drawing of the back view of the preferred embodiment of the precision alignment vacuum housing which is also the back view of the precision alignment assembly shown in FIGS. 5a and 5b.

Figure 6D:
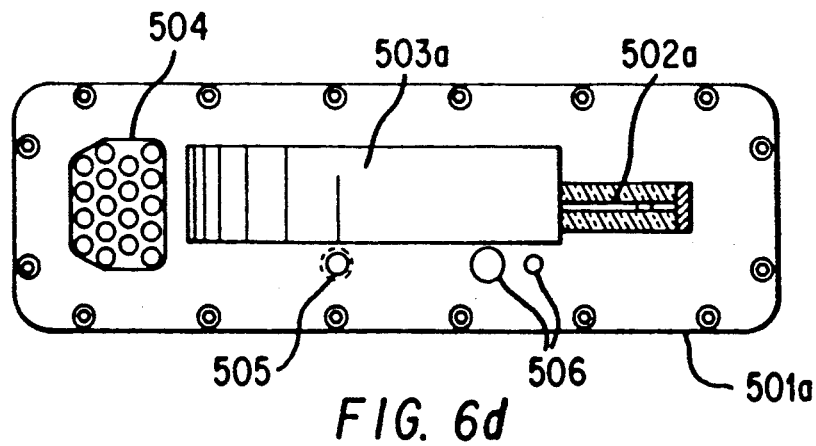
FIG. 6d is a drawing of the back view of an alternate embodiment of the precision alignment vacuum housing for use with the present invention.
Figure 6C:
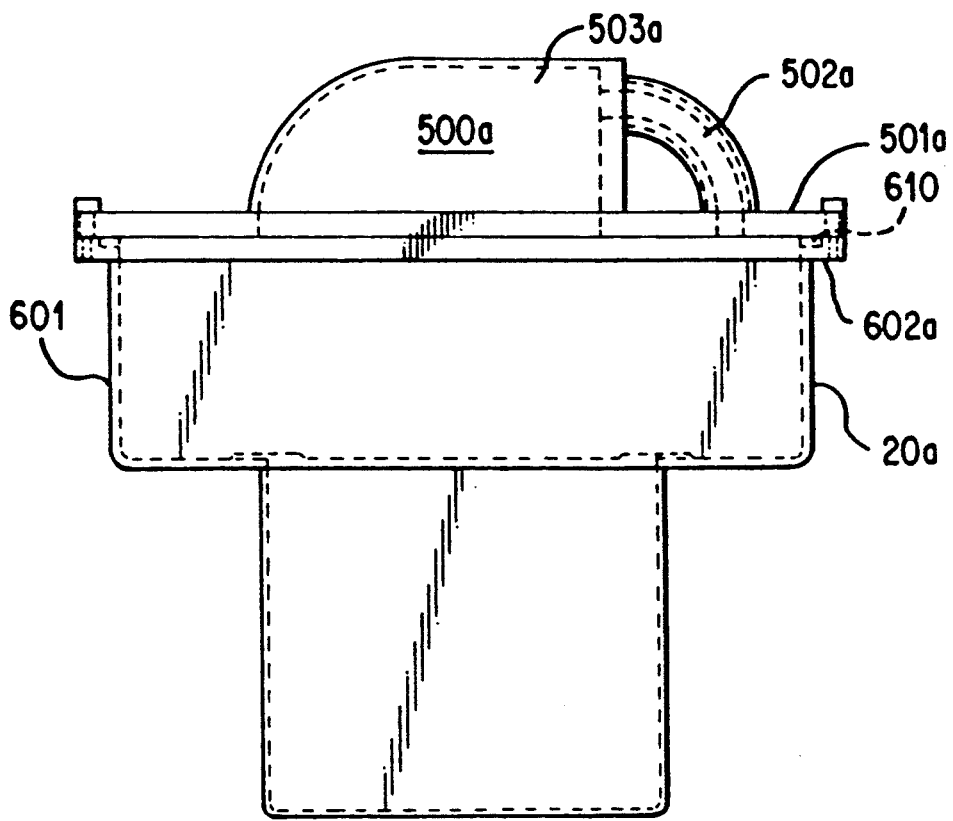
FIG. 6c is a drawing of the top view of an alternate embodiment of the precision alignment vacuum housing for use with the present invention.

FIGS. 6c and 6d show, respectively, a top view and a back view of an alternate embodiment of the precision alignment vacuum housing for use with the present invention and specifically for use with the precision alignment assembly 500a shown in FIGS. 5c and 5d. As can be seen in FIG. 6c, in the alternate embodiment in which the precision alignment plate 501a is rectangular in shape, the precision alignment assembly 500a forms the removable vacuum flange portion of the vacuum housing 20a. The precision alignment flight tube 503a is mounted to a plate section 602a at the rear of the vacuum housing. In this embodiment, the magnetic analyzer portion 502a between the analyzer magnets is made with magnetic pole pieces built into the vacuum walls to extend the north and south poles of the analyzer magnets and, thereby, decrease the effective gap inside the flight tube between the magnets and at the same time increase the magnetic flux. A seal 610 is utilized to seal the precision alignment assembly 501a to the rear plate 602a, in a manner similar to that described in connection with seal 610 of FIG. 6a. As in the preferred embodiment, the top, bottom, side and back vacuum housing walls 600 are welded, cast, or molded together to form a vacuum-tight enclosure.

Figure 7A:
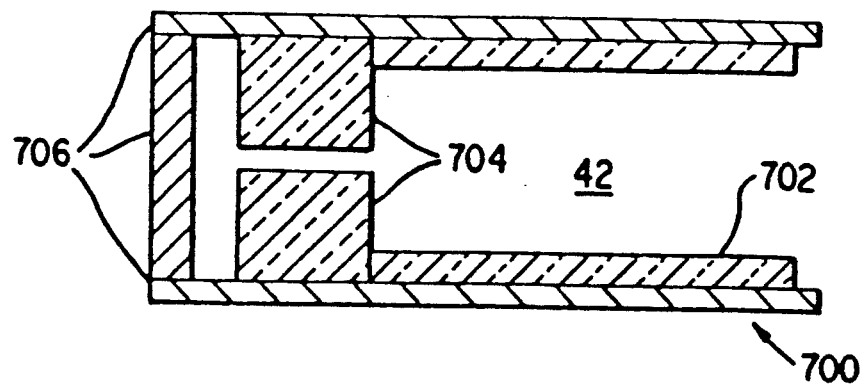
FIG. 7a is a drawing of a side view of the preferred embodiment of the magnet assembly consisting of combined analyzer and ion pump magnets and yoke for use with the present invention.
Figure 7B:
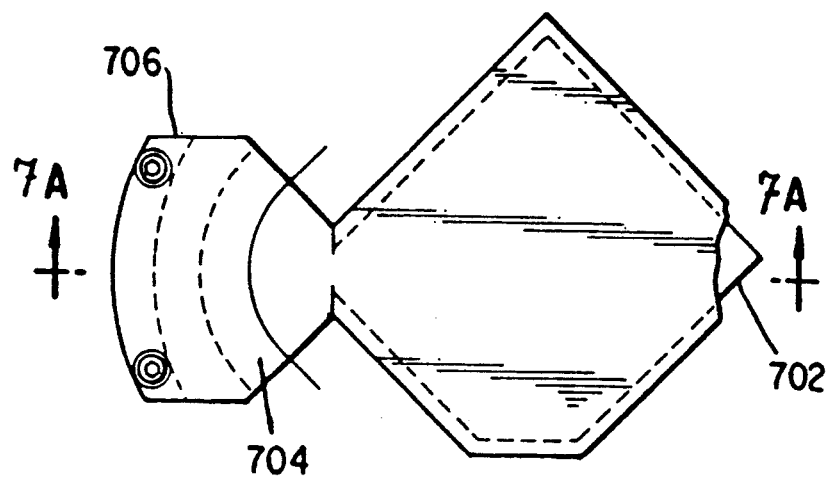

FIG. 7a shows the side view of an external magnet 700 structure designed to be mounted to the outside of the vacuum housing 20 shown in FIGS. 6a–6b. FIG. 7b shows a top view of the magnet structure which is generally U-shaped and of dimensions suitable to fit over the precision alignment vacuum housing 20. As shown in FIG. 7a, the magnet and yoke structure fits over the analyzer magnet flight tube 502 and vacuum envelope over the region of the ion pump 42 which is surrounded by the wall of the vacuum envelope 20.

The magnet assembly includes a pair of rectangularly shaped appendage ion pump magnets 702 to the inside and one end of which are mounted a pair 90° analyzer magnets 704. The two 90° analyzer magnets 704 are spaced apart in order to provide a homogenous high flux density magnetic field with a minimal gap between the two magnets. The magnet assembly is secured by a U-shaped magnetic yoke 706 whose middle portion is perpendicular to each of the appendage ion pump magnets 702 and whose two longer legs run parallel to the ion pump magnets 702.

With the magnetic structure shown in FIGS. 7a and 7b, the appendage magnets 702 are connected to the larger magnetic pole pieces or magnetic yoke 706, all of which magnets are preferably outside of the vacuum housing 20 used with the mass analyzer assembly 21. Alternatively, the appendage ion pump yoke 706 can form part of the vacuum housing 20 itself or can be inside of the vacuum housing 20. Further, the appendage magnet yoke portion of the yoke 706 can alternatively be built into the vacuum housing with a removable top plate to install the magnets, such that the yoke 706 completely surrounds the ion pump magnet and ion pump core 42, except for the internal openings 47 to conduct the gases into the ion pump cavity. This configuration has the advantage of using the surrounding yoke 706 as a magnet shield that protects the ion beam from the harmful fringing field effects from the appendage magnets 702.

With the construction of the appendage magnets 702, the 90° analyzer magnets 704 and the magnetic yoke 706 shown in FIG. 7a, the entire magnet assembly can be removed from the vacuum housing 20, leaving the vacuum housing in its sealed condition. Such a construction allows the bake-out of the vacuum housing 20 without overheating the appendage analyzer magnets 702 or the 90° magnets 704, during the bake-out. That produces the beneficial result that higher flux density magnets can be utilized for the appendage magnets 702 and the 90° analyzer magnets 704, than would otherwise be possible if the bake-out of the vacuum housing 20 occurred with these magnets 702 and 704 as part of that assembly.

An additional advantage of the magnet structure shown in FIG. 7a, besides providing a compact, high flux magnetic system, is that the same magnets 702, 704 and yoke structure 706 can be utilized to drive both the ion pump 42 and the magnetic analyzer 40.

It is preferred that the appendage ion pump magnets 702 and the 90° analyzer magnets 704 be formed of neodymium-boron-iron, available from General Motors Magnaquench Division and others. Alternatively, these magnets 702 and 704 may be of samarium-cobalt, that is more heat resistant or other high flux density materials.

Figure 7C:
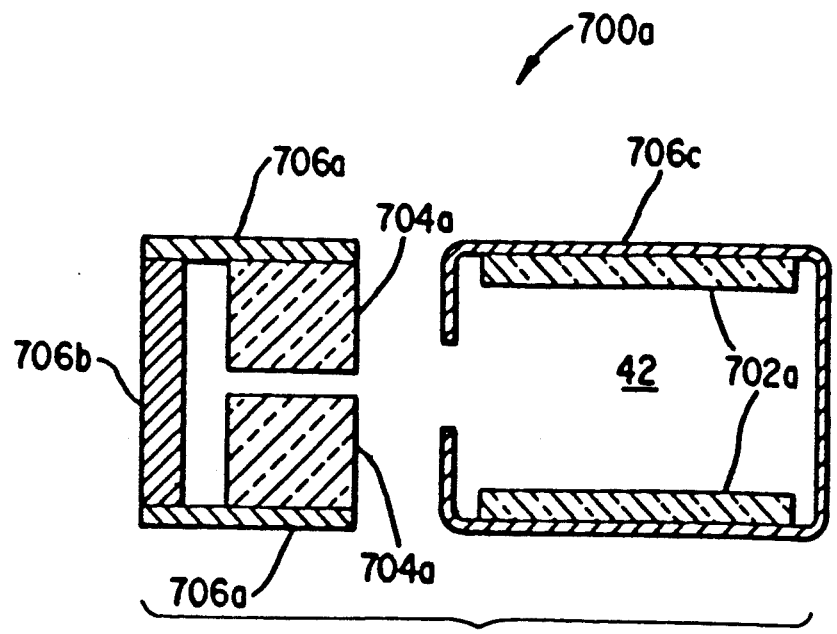
FIG. 7c is a drawing of a side view of an alternate embodiment of the magnet assembly consisting of separate analyzer and ion pump magnet and yoke for use with the present invention.
Figure 7D:
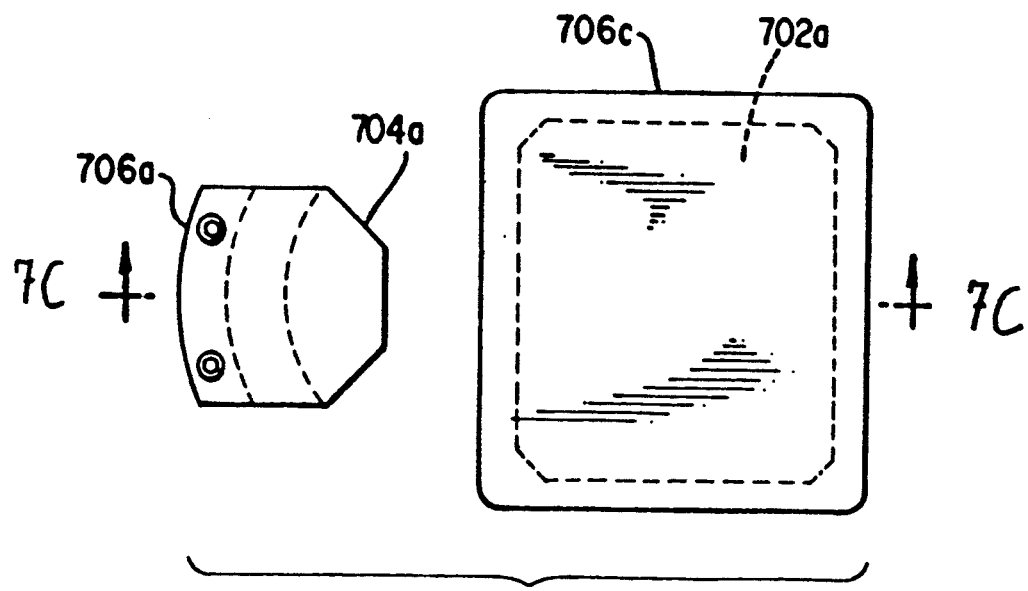
FIG. 7d is a drawing of a top view of the magnet assembly of FIG. 7c.

FIGS. 7c and 7d show an alternate embodiment of the magnet structure which may be utilized with the alternate embodiment of the mass analyzer shown in FIG. 4b. As shown in FIGS. 7c and 7d, two separate magnet sets are used to provide the magnetic fields for the magnetic analyzer 40a and the ion pump 700b. The 90° analyzer magnet is comprised of a U-shaped yoke 706a and two magnetic pole pieces 704a.

In an alternate magnet structure, the materials which form the 90° analyzer magnet pole pieces 704a and the vertical portion of the yoke 706b may be reversed such that the yoke 706b is made of high flux magnetic material, such as neodymium-boron-ion, and the balance of the yoke 706a and pole pieces 704a are made of highly permeable magnetically conducting iron, thereby creating the same type of high flux magnetic field in the gap. This configuration also permits higher temperature bake-out of the vacuum housing for short periods of time without overheating the magnetic materials. This same alternate magnet structure can be applied to the combined magnet set 700 by adding a second vertical magnet (in place of a yoke) opposite from the present vertical yoke 706.

The ion pump appendage magnet 700a is comprised of two magnet pole pieces 702a located over the ion pump 42a within the vacuum envelope 20a and a yoke structure 706c. The appendage magnet yoke 706c completely surrounds the ion pump on all sides, except for an approximately 2" diameter opening 47a into the main compartment of the vacuum housing. In that way, the appendage magnet yoke 706c acts as a magnetic shield, protecting the ion beam 39 from fringing fields produced by the appendage magnets 702a. The surrounding yoke 706c may be partially built into the walls of the vacuum housing 41a and/or attached externally around the outside of ion pump cavity.

Figure 8B:
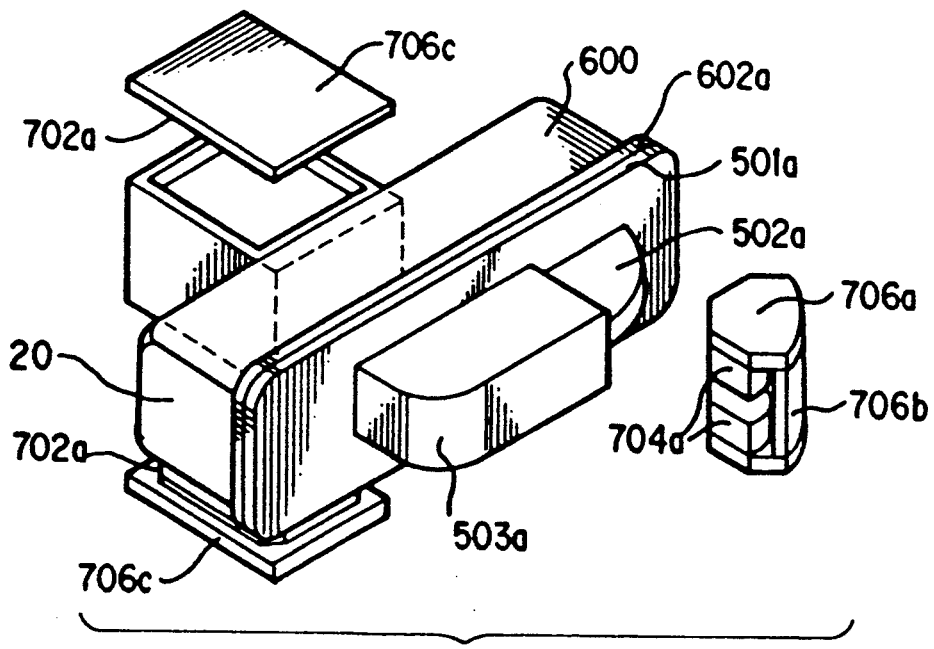
FIG. 8b is an isometric drawing of an alternate embodiment of the mass analyzer of the present invention showing the vacuum housing and magnet assembly.

The ion pump yoke side walls 41a built into the vacuum housing are shown in FIG. 4b with provisions for removal of the front wall in order to install the ion pump cell into the cavity. As shown in FIG. 8b, the U-shaped portion of the yoke 706a and the 90° analyzer magnets 704a which it carries, is mounted over the outside portion of the precision alignment flight tube 501a while the appendage magnets portion of the yoke 706c is mounted over the other side of the vacuum envelope 20a such that it is located directly over the ion pump 42a.

Figure 8A:
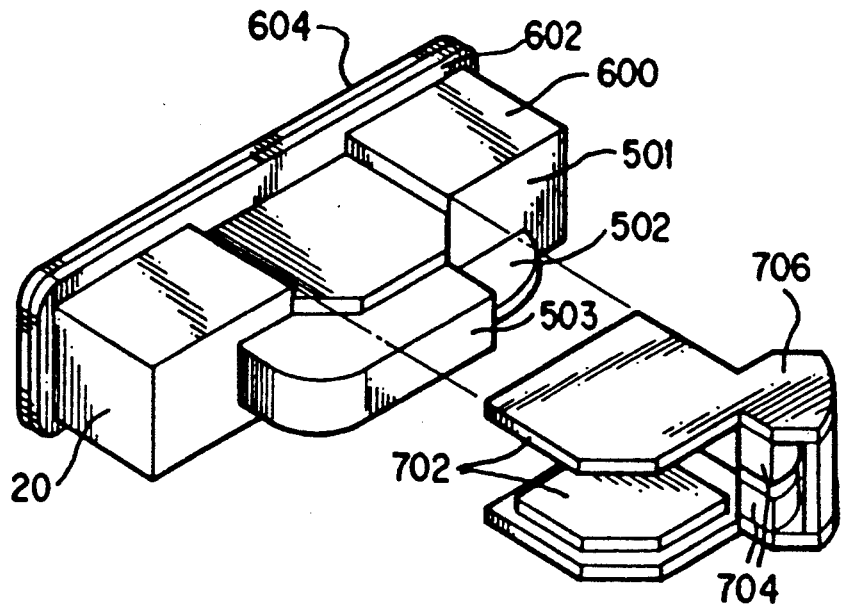
FIG. 8a is an isometric drawing of the preferred embodiment of the mass analyzer of the present invention showing the vacuum housing and magnet assembly.

FIGS. 8a and 8b are isometric drawings of the preferred and alternate embodiments, respectively, of the mass analyzer of the present invention and show the vacuum housing and magnet assembly.

Figure 9B:
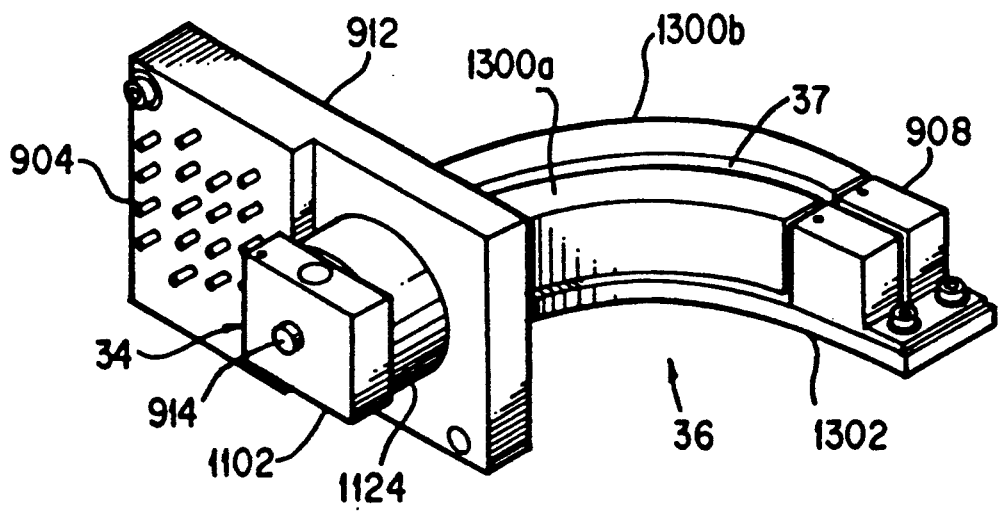
FIG. 9b is an isometric drawing of the ion source and the electric sector assembly showing the ion source mounting plate and electric feedthrough connections for use with the present invention.
Figure 9A:
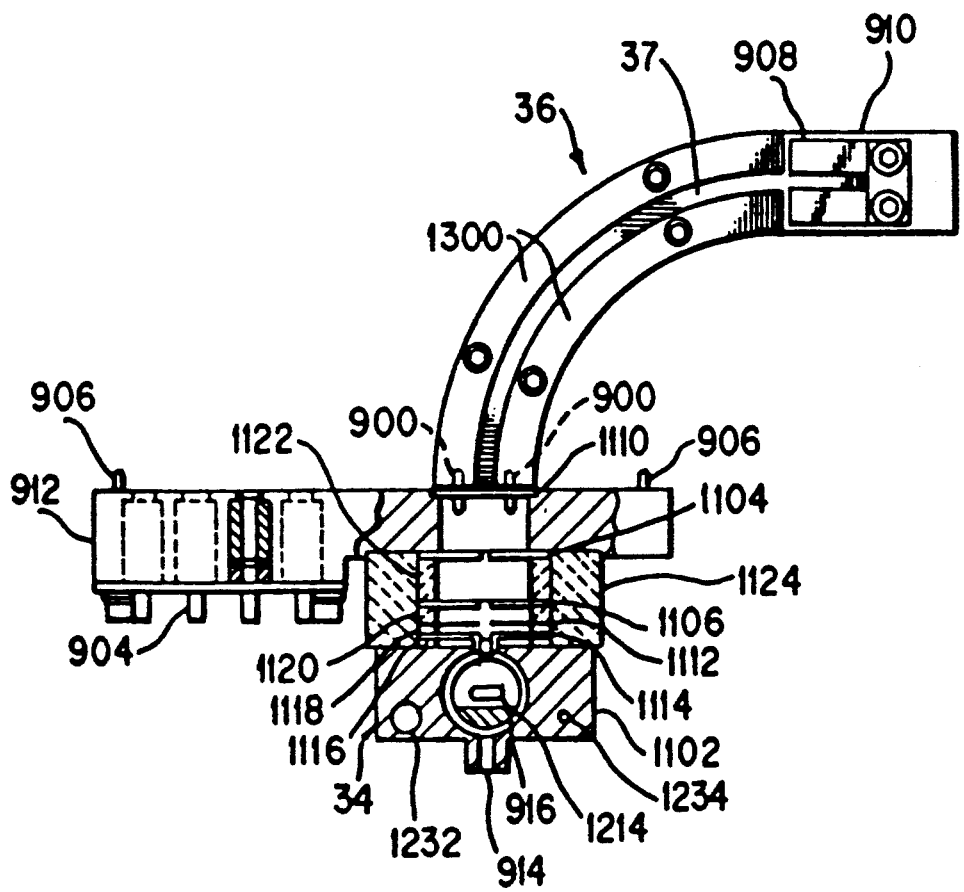
FIG. 9a is a drawing of a top view of the ion source and electric section assembly for use with the present invention.

FIG. 9a is a drawing of the top view of the ion source 34 and electric sector assembly 36 for use with the magnetic analyzer 21 of the present invention. FIG. 9a shows the details of the ion source 34 as well as the details of the mounting of the electric sector 36 to the ion source mounting plate assembly 912 such that the electric sector 36 is precisely aligned with the ion source 34 by means of alignment pins 900 and fasteners (not shown).

The ion source 34 includes a block assembly 1102 to which the remaining components of the ion source 34 are secured. The block assembly 1102 provides the alignment mechanism for the components of the electron gun assembly and the ion beam lens assembly and contains the ion source filament and the inlet 914 for receiving the sample from the membrane separator 16a. The ion source assembly 34 functions to accelerate and form a beam of nearly monoenergetic ions that are created in the ion source 34 by electron impacts at 70 eV.

A cylindrical housing 1124 is used to align and secure the lens elements of the ion source assembly 34. The bottom of the cylindrical housing 1124 rests upon the block assembly 1102. Inside the cylindrical housing 1124, a first cylindrical spacer 1116 is used to separate the saddle lens 1114 from the surface of the block assembly 1102. A second circular spacer 1118 rests on the saddle lens 1114 and spaces it away from a split lens 1112. A third cylindrical spacer 1120, which is several times thicker than either of the first and second cylindrical spacers 1116 and 1118, rests upon the split lens 1112 and separates it from the object plate 1106. A fourth spacer 1122, which is several times thicker than the third spacer 1120, is used to space the object plate 1106 away from the collimating slit lens 1104, and is configured such that the collimating slit lens 1104 is flush with the outside upper surface of the cylindrical housing 1124. The insulating spacers are made of Macor or similar machinable glass ceramic except for the spacer 1122 which is a conducting material, such as gold-plated stainless steel, while the lenses are preferably gold-plated stainless steel in order to reduce the interaction of the sample with the metal lenses, thus decreasing the strength of the ion beam.

A mounting plate 912, rests upon the upper surface of the cylindrical housing 1124 and is attached to the block assembly 1102 by four insulated screws. An entrance slit and electric shunt plate 1110 is secured to that plate 912 in such a manner that the upper surface entrance slit 1110 is flush with the upper surface of the ion source mounting plate 912.

The ion source mounting plate 912 includes two alignment holes (not shown) into which two alignment pins 900 of the electric sector 36 are inserted in order to align the electric sector 36 to the ion source mounting plate 912. The ion source 34 is also precisely mounted to the ion source mounting plate 912 such that the ion source 34 and the electric sector 36 are precisely aligned with respect to each other so that the ion beam generated within the block assembly 1102 of the ion source 34 passes through each of the electrically charged lenses 1114 and 1112, in turn. The ion beam passes through the slits 1106 and 1104 and the entrance slit 1110 into the electric sector 36, and is maintained within the electric field 37 created between the two plates 1300 of the electric sector 36. It then passes through the exit shunt 908 of the electric sector 36.

A plurality of electric feedthrough connector pins 904 are located on the front side of the ion source assembly plate 912. Two alignment pins 906 are located on the opposite side, such that the electric sector 36 and ion source 34 assembled to the ion source assembly plate 912 may be readily aligned to the precision alignment plate 501 which includes corresponding alignment holes (not shown).

FIG. 9b is an isometric drawing of the ion source 34 and electric sector 36 assembly mounted to the ion source mounting plate 912 and shows in greater detail the plurality of electric feedthrough connector pins 904.

Figure 10:
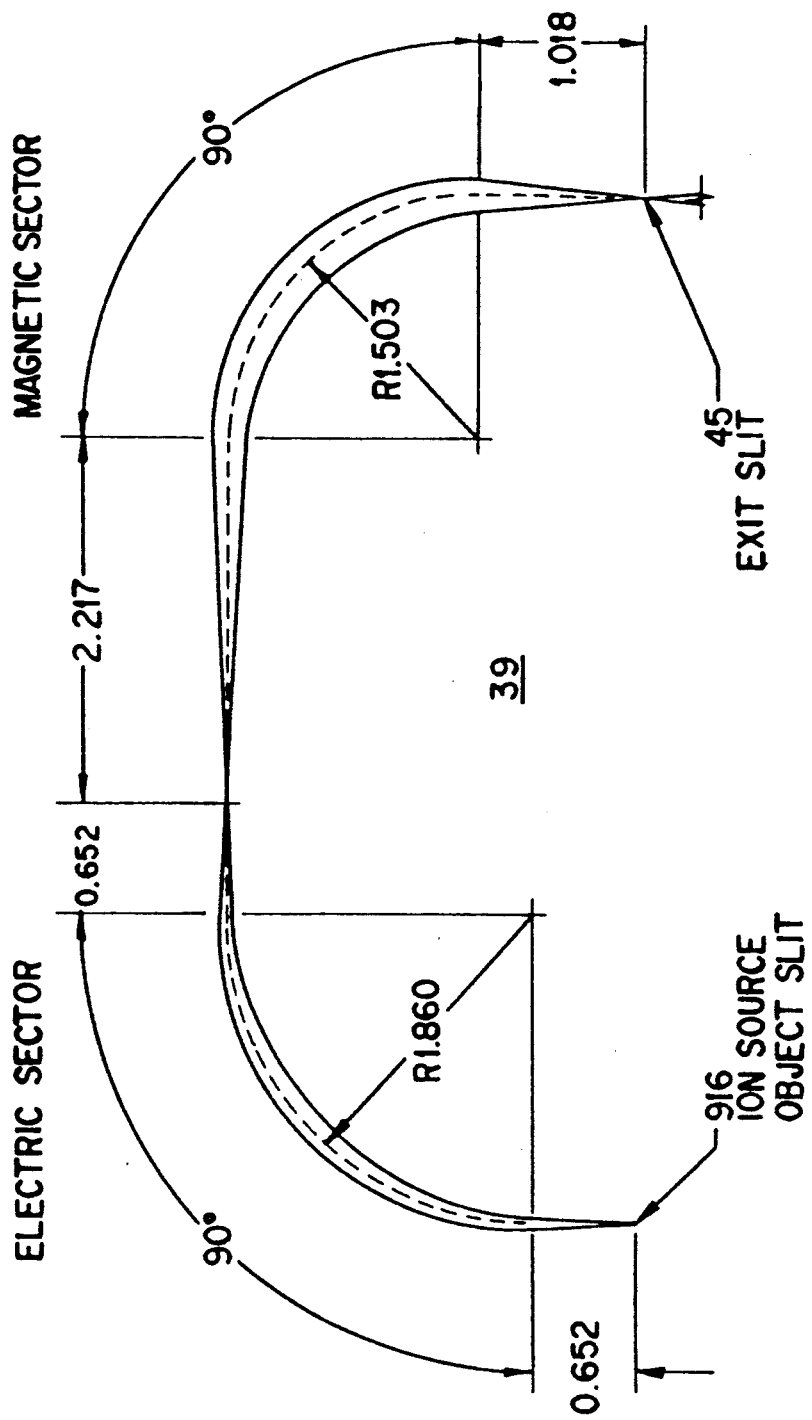
FIG. 10 is a schematic drawing of the path of the ion beam generated by the mass analyzer of the present invention.

FIG. 10 is a schematic drawing of the preferred path 39 of the ion beam generated by the mass analyzer 21 and shows the path of the ion beam from the ion source object slit 916 through the electric sector 36 and the magnetic sector 40 and onto the exit slit 45 of the ion detector 44. Alternatively, other ion optics geometry may be utilized to optimize the desired performance characteristics of the mass spectrometer.

Figure 11C:
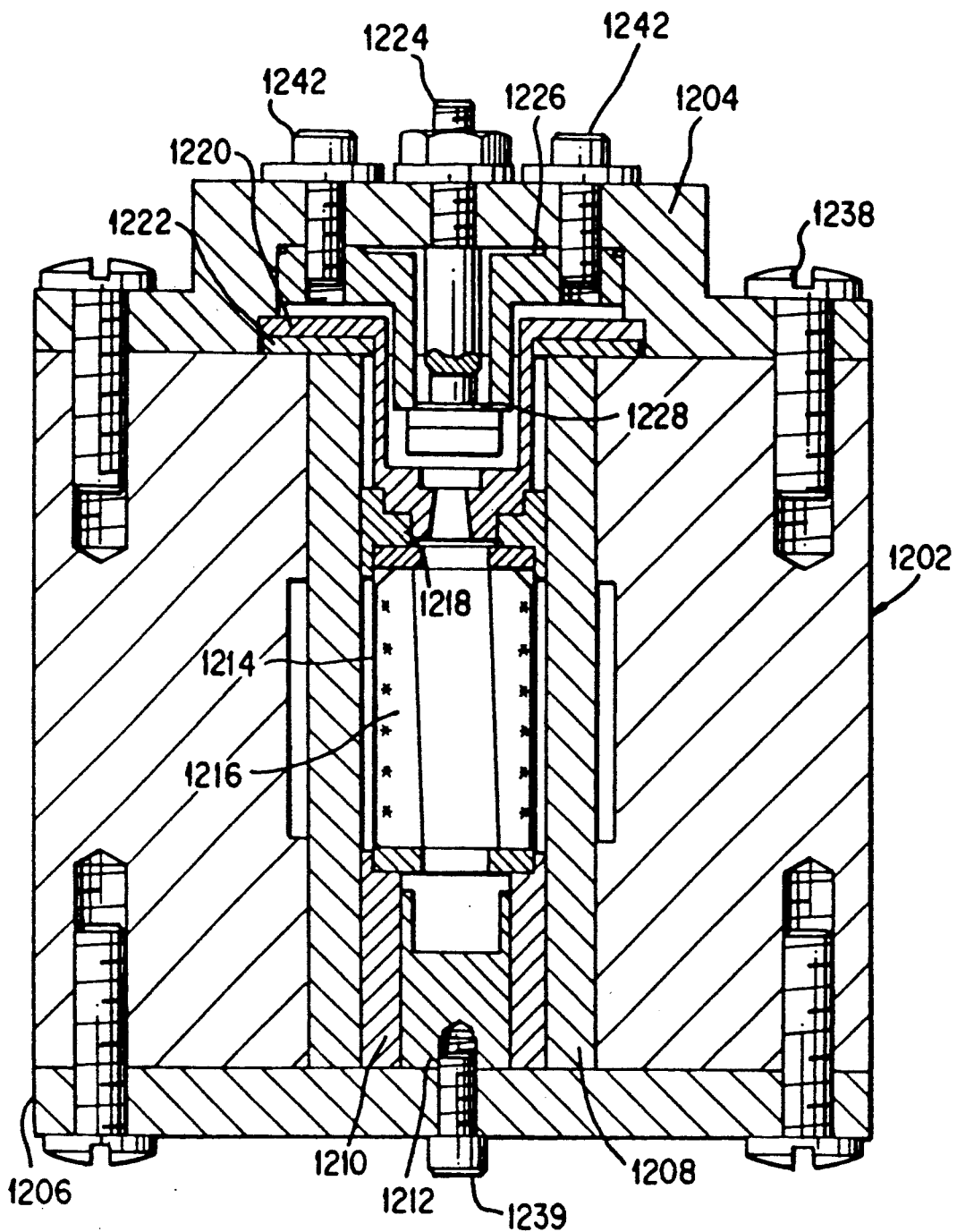
FIG. 11c is a drawing of a section taken along the line D—D of FIG. 11b of the block assembly of the present invention.
Figure 11D:
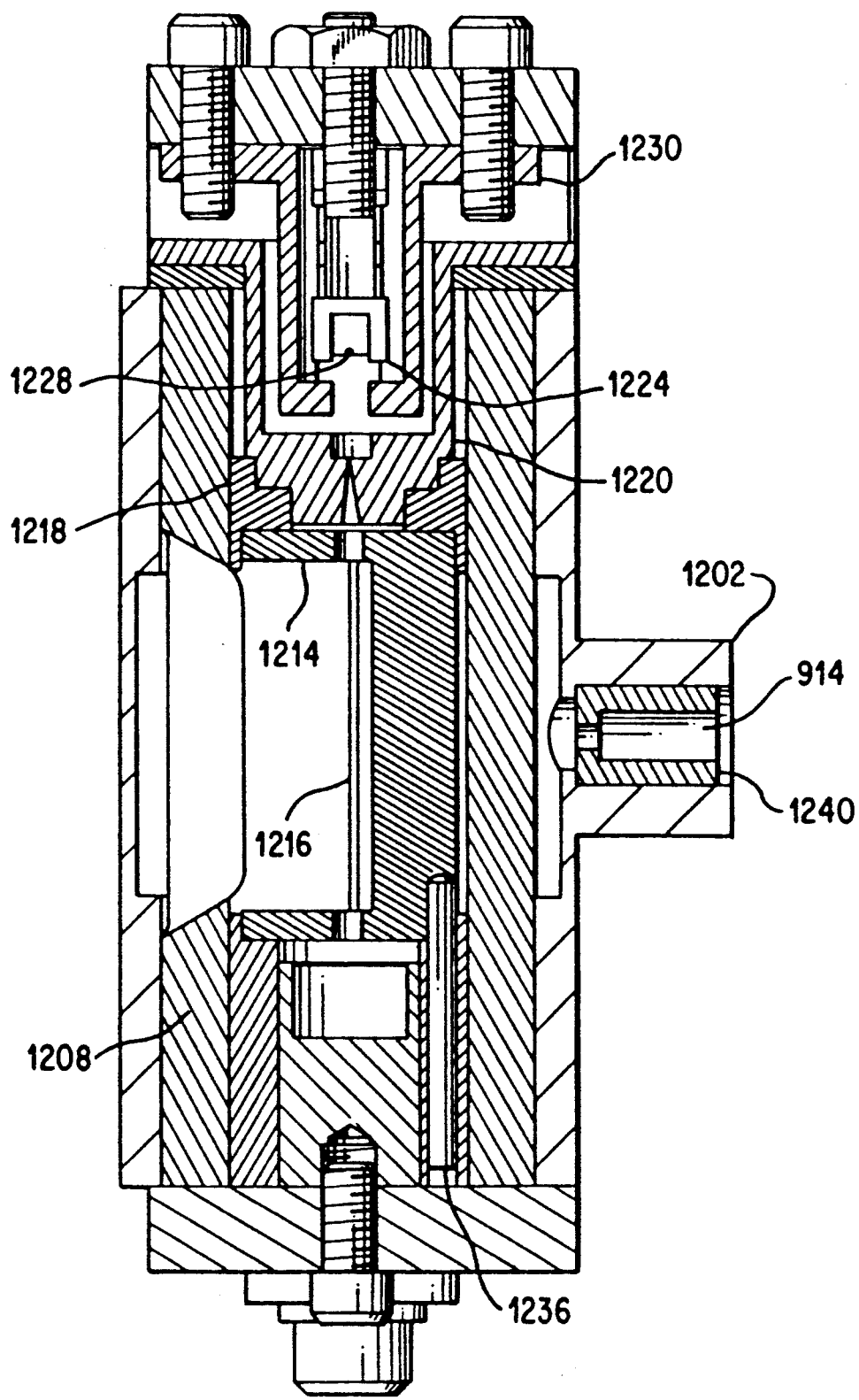
FIG. 11d is a drawing of a section taken along the line B—B of FIG. 11a of the block assembly of the present invention.

FIGS. 11a–11d show the block assembly 1102 used with the ion source assembly 34. FIG. 11a shows a front view of the block assembly while FIG. 11b shows a side view of that same block assembly 1102. FIG. 11c shows a section along the line D—D of FIG. 11b of the block assembly 1102. The function of the block assembly is to provide a central alignment point for both the electron gun assembly and the ion beam lens assembly. It is heated to reduce sample loss.

FIG. 11c is a drawing of a section along the line D—D of FIG. 11b. The block assembly 1102, as shown in FIG. 11c, includes a block 1202 which is generally rectangular in shape and contains a hollowed out center portion. Mounted to the top of the block 1202 is a filament cap 1204 in which the filament 1228 is secured, as will be described later hereinafter. Mounted to the bottom of the block 1202 is an anode cap 1206, which forms the anode portion of the block assembly 1102 and of the ion source 34.

Secured within the center of the block 1202 is a cylindrical magnet 1208 which extends the entire length of the block 1202. At the bottom portion and inside the cylindrical magnet 1208 is a cylindrical anode spacer 1210 which surrounds the anode 1215 itself. A fastener 1239 is used to connect the anode to the bottom cap 1206 of the block 1202 and passes through the anode cap 1206. A repeller 1214 is mounted inside the cylindrical magnet 1208 such that it rests in a circular step formed at the top of the spacer 1210. The repeller is insulated from other components of the ion source and functions to eject the positive ions created into the accelerating field. The repeller 1214 contains a repeller insert 1216 whose function is to improve the shape of the ion beam and reduce its energy spread. The repeller insert 1216 is welded to the repeller 1214.

A circular filament space 1218 is located at the top of the repeller 1214 and serves to space the repeller 1214 away from the inside wall of the circular magnet 1208. A slit plate 1220 of generally conical shape is placed in an inverted fashion such that it fits into the filament spacer 1218. A second filament spacer 1222 is located between the bottom cylindrical portion of the generally conically shaped slit plate 1220 and the top of the block 1202 and spaces the bottom portion of the slit plate 1220 away from the top edge of the block 1202.

The filament 1228 is mounted to the filament cap 1204 by means of two circular filament mounts 1226 which is secured by two bolt and nut combinations 1242 to the upper inside surface of the filament cap 1204. A filament shield 1224 is located directly above the filament 1228 in order to improve the flow of electrons into the ion chamber. The filament cap 1204 is secured to the block 1202 by a plurality of cap bolts 1238.

Referring now to FIG. 11e, there is shown a section taken along the line A—A of FIG. 11a. As shown in FIG. 11e, the ion source assembly 34 is heated by means of a cartridge heater 1232, which may, for example, be model number SC181, available from Scientific Instrument Services, Inc. Alternatively, part number 40003-48020, available from Finnigan Corporation of Sunnyvale, Calif. may also be utilized.

FIG. 11f shows a section along the line C—C of FIG. 11a. As shown in FIG. 11f, a thermocouple 1234, which may be part number PT-B, available from Scientific Instruments, Inc., may be utilized to sense the temperature of the block.

Figure 12B:
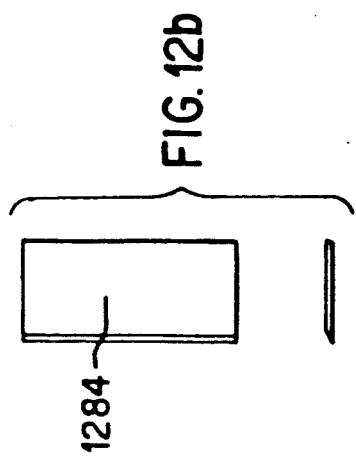
Figure 12C:
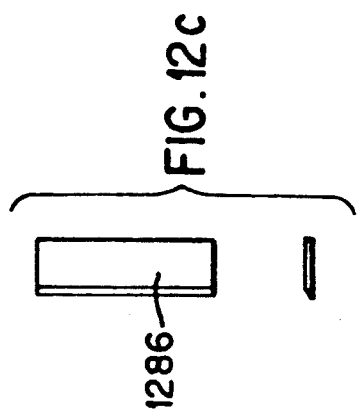
Figure 12A:
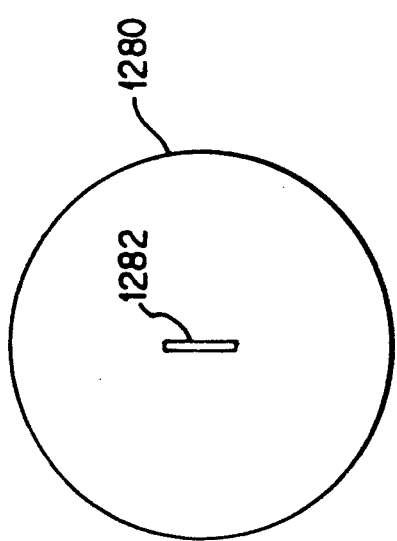
FIG. 12a is a drawing of the top view of a mounting disk which carries a lens assembly used with the ion source for use with the present invention.
Figure 12D:
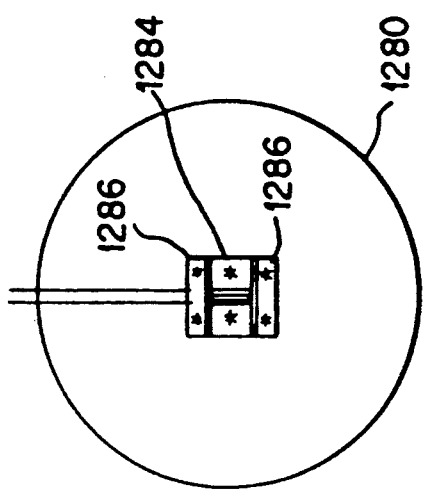
FIG. 12d is a drawing of a top view of the lens assembled from the components shown in FIGS. 12a-12c.

FIGS. 12a–12d show the details of the formation of a lens which form part of the ion source 34, as previously described. The example shown in FIG. 12a is the collimating lens mounting plate.

As shown in FIG. 12a, a mounting disk 1280 formed from an electrically conductive metal, such as stainless steel, is machined such that a slit 1282, of appropriate dimensions, is formed in the center thereof.

As shown in FIGS. 12b and 12c, the large blade 1284 and small blade 1286 are formed of generally rectangular shape and beveled at an angle of approximately 45° on one of the longer edges thereof. The blades 1284 and 1286 may preferably be made from an electrically conductive metal, such as stainless steel. In order to fashion the lens, a pair of large blades 1284 and a pair of small blades 1286 are either permanently or adjustably affixed to the mounting plate 1280 such that they surround the slit 1282 and form a slit of the desired dimensions therebetween. Alternatively, the lens slits may be directly machined into a blank disk 1280 by using new precision fabrication methods such as a wire or conventional electric discharge machine (EDM) using a specially designed EDM "sinker" or cutting tip for this purpose.

Figure 13A:
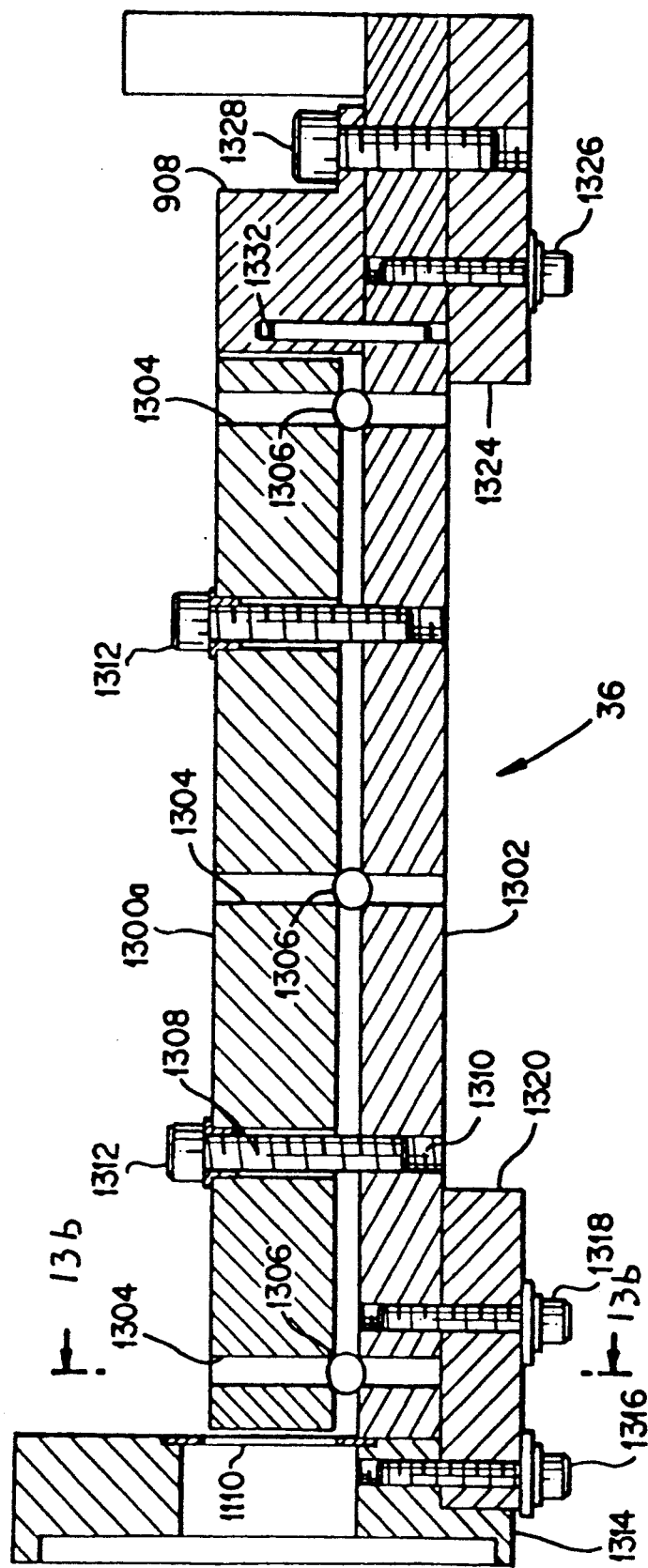
FIG. 13a is a drawing of a side view of the electric sector assembly for use with the present invention.
Figure 13B:
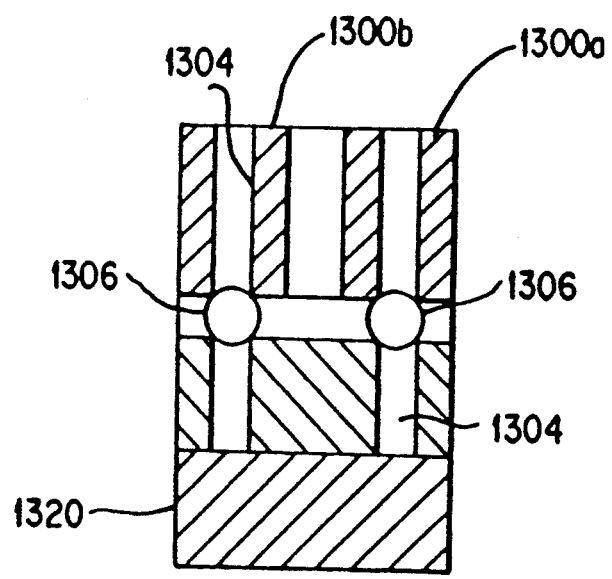
FIG. 13b is a drawing of a section taken along the line A—A of FIG. 13a of the electric sector assembly.

FIGS. 13a–c show drawings of the electric sector assembly 36 for use with the present invention. FIG. 13a is a side view of the electric sector assembly 36 whose major components are an electric sector plate 1302 to which is mounted two sectors 1300, such that the two sectors are precisely parallel, spaced apart from each other and form an angle of exactly 90° with respect to the electric sector plate 1302.

In order to accomplish the exact alignment required in order for the electric sector assembly 36 to function properly, the electric sector plate 1302 and both of the sectors 130 have drilled in them, in corresponding locations, a plurality of bore holes 1304. Between the corresponding bore holes formed in the electric sector plate 1302 and the two sectors 1300a and b, a corresponding number of ruby sapphire spheres 1306 are located.

Each of the sectors 1300 also contains a plurality of bores 1308 which correspond to threaded holes 1310 formed in the electric sector plate 1302. A corresponding plurality of securing devices, such as cap bolts 1312, are inserted through the bore 1308 in each of the sectors 1300 separated electrically from the sectors by insulating washers 1301 and threaded into the threaded bores 1310 contained in the electric sector such that, when tightened, each of the sectors 1300 is automatically secured to the electric sector plate 1302 in a precisely orthogonal configuration. The sectors 1300a and b are also aligned precisely parallel to each other.

In addition to serving as the means of aligning the sectors 1300 to each other and to the electric sector plate 1302, the ruby sapphire spheres 306 serve to space each of the sectors 1300 away from the electric sector plate 1302 as well as to electrically insulate each of the sectors 1300 from the electric sector plate 1302.

In order to secure the electric sector assembly 36 to the ion assembly 34, a cap assembly 1314 is secured by means of two cap bolts 1316 and 1318 to an entrance bracket 1320. One bolt 1318 secures the entrance bracket 1320 to the electric sector plate 1302, near the entrance end thereof. The other bolt, element 1316, bolts the cap assembly 1314 to the entrance bracket 1320. The cap assembly 1314 also includes an entrance shunt slit 1110 which is mounted at the entrance end of the sectors 1300 and electric sector plate 1302 in such a manner that it terminates the electric field and avoids fringing field perturbations of the ion beam.

FIG. 13b shows a section along the line A—A of FIG. 13a and more clearly shows the structure of the electric sector 36 in which the electric field 37 is created.

The electric sector assembly 36 also includes an exit bracket 1324 which is used to secure the exit end of the electric sector assembly 36 within the precision flight tube 503. The exit bracket 1324 is secured to the bottom of the electric sector plate 1302 by means of two cap bolts 1326 and 1328. An exit shunt 908, which also functions to reduce fringing field effects, is located at the exit end of each of the sectors 1300. It is secured as part of the electric sector assembly 36 by means of the cap bolt 1328.

FIG. 14 is a schematic diagram of the sample inlet and concentration assembly 12 and the gas chromatograph assembly 14 and shows the sample flow layout used by the miniaturized mass spectrometer system 10 of the present invention. These assemblies are designed to allow operation of the mass spectrometer system 10 in a plurality of modes described later herein. The gas flow system includes a valve 1402 which is connected to receive the input from the atmospheric inlet port 228. In addition, as previously described, a sample may be injected into the injector 216. All of the valves and sample lines shown in FIG. 14 are heated to approximately 50° C. to prevent the sample from condensing within the valves and sample lines. All of the heated components are enclosed within an insulated area or thermal zone 1400 to prevent heat losses and to conserve power.

The injector 216 is connected directly to the input of the gas chromatograph 14 whose output is connected to the input of the membrane separator 16a. The output from the membrane separator 16a, as previously described, goes to the inlet 914 of the ion source 34. A sampling pump 206 is also connected to the membrane separator 16a, through a valve 1416 such that, when the pump is on and the valve 1416 is in its normally closed position, a vacuum suction is created in the membrane separator 16a, for purposes which will be described later herein.

The atmospheric inlet port 228 is connected through two valves 1402 and 1406 to various portions of the sample flow system of the present invention. Through the set of valves 1402, 1406, when in their appropriate positions, the sample enters the miniaturized mass spectrometer system 10 of the present invention through the atmospheric inlet port 228 and is conducted directly to the input of the membrane separator 16a. As will be described herein, sampling pump 206 is utilized to assist in that process. Alternatively, the sample which enters through the valves 1402 and 1406 may be directed, by the appropriate placement of the valve 1406, through an enrichment cartridge 214 which may or may not be heated by a heater 1414 and then through another valve 1412 to the input to the membrane separator 16a. The second set of valves 1404 and 1408 are used to input a carrier gas from a carrier gas cylinder 200 into the system, as will be later described.

As previously stated, the present invention is capable of operating in at least five cycles. In the first cycle, which is termed the direct mass spectrometry or direct MS cycle, an atmospheric sample enters, through inlet port 228, the first valve, 1402 which is normally open and then passes through the third valve 1406, which is normally closed, thus sending the sample directly to the input of the membrane separator 16a. By means of the sampling pump 206 and the valve 1416, which is moved to its on position, a suction is provided through the membrane separator which serves to cause the sample to flow into the input of the membrane separator 16a.

In a second cycle of operation of the instant miniaturized mass spectrometer system 10, termed the enriched mass spectrometry or enriched MS cycle, the sample is again input through the inlet port 228 and valve 1402 through the third valve 1406, which is in its normally closed position such that the sample flows through the enrichment cartridge 214, through the fifth valve 1410 and sixth valve 1412 and out through the seventh valve 1416, by means of the suction created by the sampling pump 206. That portion of cycle 2 is termed the adsorb cycle.

The second subcycle of the enriched MS cycle is a desorb cycle. The carrier gas enters the miniaturized mass spectrometer system 10 of the present invention by means of the second and fourth valves, 1404 and 1408, which are positioned such that the gas is directed to the input side of the enrichment cartridge 214, flows through the enrichment cartridge and is heated by the enrichment cartridge heater 1414. The enriched sample flows through the fifth valve 1410 and the sixth valve 1412, which are positioned such that the sample then flows directly to the input of the membrane separator 16a. The sampling pump 206 is not operated in this cycle, however, the seventh valve 1416 is placed in the on position such that the membrane separator 16a is vented to the outside atmosphere at the exit side of the sampling pump 206.

In a third cycle, termed the direct injection cycle, the sample is injected by a syringe into the injector port 216 while a carrier gas enters the system by means of the second valve 1404 and fourth valve 1408, which are positioned such that the carrier gas enters the injector 216 from the output of the fourth valve 1408. The injector heater 1422 is operated in a heat soaking manner. The injected sample enters into the gas chromatograph system 1410 whose heater 1424 is operated in a programmed manner, as will later be described. The sample then passes from the output of the gas chromatograph to the input of the membrane separator 16a. In this cycle, the sampling pump 206 is again not operated and the seventh valve 1416, is placed in its on position so that the membrane separator 16a can be vented to the outside atmosphere.

In a fourth cycle, termed the enriched GC/MS cycle, there are three subcycles. In the first subcycle, termed the sample subcycle, the sample is input through the inlet port 228 and the first and third valves 1402 and 1406 to the input of the enrichment cartridge 214 whose heater 1414 is not turned on. The sample flows out through the fifth and sixth valves 1410 and 1412 and is directed through the seventh valve 1416 and out into the atmosphere, by the operation of the sampling pump 206.

In the second subcycle of the enriched GC/MS or gas chromatograph mass spectrometer cycle, termed the cold flow subcycle, the carrier gas is input through the second and fourth valves 1404 and 1408 to the input of the enrichment cartridge 214. Again, the enrichment cartridge heater 1404 is not turned on. The carrier gas flows through the closed valves five and six, 1410 and 1412, and out through the closed seventh valve 1416 and the nonoperating sampling pump 206 into the atmosphere.

In the final subcycle of the enriched GC/MS cycle, termed the desorb subcycle, the carrier gas again passes through the open valves two and four, 1404 and 1408, and through the enrichment cartridge 214, whose enrichment heater 1414 is operated in a ballistic mode. The sample then passes through the open fifth valve 1410, and through the injector 216 whose heater 1422 is operated in a soak mode and then to the input of the gas chromatograph 14. The gas chromatograph heater 1424 is operated in a programmed mode. The output of the gas chromatograph 14 is passed to the membrane separator 16a. The membrane separator is open to the atmosphere by means of the on or open seventh valve 1416 and the non-operating sampling pump 206.

FIG. 15 shows a block diagram of the microcomputer 24 and control electronics 28 utilized with the present invention. The microcomputer 24 and control electronics 28 are organized around a microprocessor bus 1501, which may also be a multiprocessor bus. As previously described, the microprocessor bus 1501 may be contained within a readily available IBM compatible AT or PS/2, or higher class personal computer. As is well known in the art, the bus is utilized to transfer instructions, data and other information between the various components of the microcomputer 24. For example, a CPU 1500 is connected to transmit and receive information from the bus 1501, as is a memory RAM 1502 and an EPROM 1504. If desired, the on-board operating system of the microcomputer system 24 for the mass spectrometer system 10 of the present invention may be stored in the EPROM 1504 or ROM 1510.

The on-board microcomputer 24 is provided with additional storage space by means of a solid state storage device 226, which is preferably a card containing a plurality of battery-backed dynamic random access memory (DRAM), static RAM (SRAM) or read only memory (ROM). In addition to containing the operating instructions for controlling the functions of the mass spectrometer system 10, the removable solid state storage device 226 can also be used to store other data and information. Since the solid state storage device 226 may be readily inserted and removed from the microcomputer portion 24 of the mass spectrometer system 10, it can be utilized to provide software and system updates in an easy, inexpensive and known manner. The solid state storage device 226 is connected to the microprocessor bus 1501 by means of a data storage interface 1506.

The mass spectrometer system 10 of the present invention, as has been described, carries its own library of the mass spectra of known compounds of which the mass spectrometer is expected to be testing and which need to be identified by matching the unknown spectra with the library of known spectra. Inasmuch as there is a generally predetermined number of environmental compounds for which it is conceivable the present mass spectrometer system 10 will be utilized to identify, the library may be stored in read only memory devices (ROM), including the software program for matching unknown environmental samples to be identified with the library of known mass spectra.

An LCD display 218 is also connected to the microprocessor bus 1501, by means of an LCD display driver 1512, in a known fashion. In addition, the mass spectrometer system 10 of the present invention may also be provided with a visual and audible alarm 1510, which is also connected to the LCD display driver 1512, in order to receive signals from the microprocessor bus 1501. Other audio and visual indicators 1516 are provided, including LED displays 230 that are used as visual indicators of system status.

As has been described, the mass spectrometer system 10 of the present invention may be utilized to receive control signals and other data and information by means of radio wave transmissions or through land or other lines utilizing modems or other signal converting mechanisms. Thus, telemetry and communication ports 1518 are provided which are connected to the microprocessor bus 1501. In the event that it is desired to either send or receive data, information or instructions to or from the mass spectrometer system 10 of the present invention, an external portable microcomputer with integral display 1520 can be utilized, in a known fashion.

In order to control the operation of the GC/MS or tandem mass spectrometer (MS/MS), various control signals are provided, under the control of the CPU 1500. In order to automatically effectuate such control, the signals generated onto the microprocessor bus 1501, either from the CPU 1500 directly or from one of the memories 1502, 1504 or 226, are converted from digital to analog signals by means of the digital-to-analog converter 1524 which is also connected to the microprocessor bus 1501, and then fed to the GC/MS or MS/MS as either a control signal or an electric sector sweep control signal, as will be described later herein. The electric sector sweep feedback signal and system diagnostic signals are fed by means of an analog-to-digital converter 1522 back onto the microprocessor bus 1501, for diagnostic and control reasons. In addition, the data output from the ion detection system 44 is also converted from an analog to a digital signal by means of the A/D converter 1522 and thence onto the microcomputer bus 1501 from where such information may be taken and analyzed, as will be described later herein.

The microprocessor 24 of the mass spectrometer system 10 of the present invention also includes a plurality of digital or parallel input/output interfaces 1526 and 1528, which are utilized to control, by means of electromechanical devices, many of the functions of the mass spectrometer system 10 of the present invention. Thus, connected to the parallel I/O interfaces are such features as the power shutdown control 1532, the turning on and off electric heaters such as heaters 1414, 1422 and 1424, the operation of the sampling pump 206 used with the sample concentrator 12, the operation of the cooling fan 224 used with temperature sensors to control interior temperatures of the system 10 and the operation of the various relays and valves commonly used with a GC/MS or MS/MS, as is known in the art. In addition, signals received from alarm detectors and switch monitors are also input into the parallel I/O interface for transmission to the microprocessor bus 1501. The operation of the various keyboard 220 and/or function keys 1630 is also input onto the microprocessor bus 1501 by means of the parallel input/output interface 1526, 1528.

FIG. 16 shows the functional flow chart of the operation of the software resident in the microcomputer 24. The software is utilized to operate and monitor the mass spectrometer system 10 of the present invention.

As shown in FIG. 16, there are six major functions of the software that are well known in the art: manage the power and vacuum of the mass spectrometer 1600, manage the external interfaces 1602; control and monitor the cycles of the GC/MS instrument 1604, control the mass spectrometer and process the mass spectrometer data 1606, analyze the mass spectrometer data 1608 and maintain the health of the GC/MS instrument 1610.

The basic software functions to control the mass spectrometer and analyze the mass spectra data represented by parts of 1602, 1604, 1606, 1608 are available from commercial suppliers of mass spectrometer data systems such as the Shrader System™ distributed by Vacumetrics, Inc. of Ventura, Calif. or Vector/One GS/MS software system produced by Teknivent Corp. of St. Louis, Mo. These commercial software packages operate under MS-DOS directly on IBM-AT compatible computer systems or may be adapted to other suitable real-time operating systems used for the microcomputer 24 of the instant mass spectrometer system 10.

Each of those functions, together with the mass spectrometer data provided to the GC/MS instrument and the mass spectrometer signature library data 1612, which, as previously described, may be stored in the ROM library 1510 or may also be stored in other provided memory devices, for example, the solid state storage device 226 or the EPROM 1504, are utilized to operate the mass spectrometer system 10. As shown in FIG. 16, each of the control functions 1600–1610, are interconnected.

In order to manage the power and vacuum, the power and vacuum manager 1600 monitors the input of both DC power (in the case of the preferred embodiment of the mass spectrometer system 10) and the on-board computer on and off control. The manage power and vacuum function 1600 sends a power/vacuum status message to the manager of external interfaces 1602 as well as transmits the power/vacuum data/status signal to the maintain health of instrument function 1610. The manage power and vacuum function 1600 also allocates the available power to the various devices by means of a signal sent to the control and monitor instrument cycles function 1604. Finally, hardware indicators, such as power status and battery warning LEDs, are sent by the manage power and vacuum function 1600.

The external interface manager 1602 manages the input and output of information to the user and external devices including the LCD display, keyboard, printers, modems and other means. The external interfaces manager 1602 receives inputs from the user or on-board computer 24, receives a data input from a user or an external source and receives an input from a user or an external device. The external interfaces manager 1602 provides output signals to the user display or on-board computer 24, provides a data output to an external computer, provides an output to an external device and also provides an output to an external printer and other devices.

The manager of external interfaces 1602 also serves to control the instrument cycles of the mass spectrometer instrument system 10, by means of its communication with the control and monitor instrument cycles function 1604. It also controls the mass spectrometer data analysis by means of its communication with the mass spectrometer data analyzer function 1608.

Other inputs to the external interfaces manager 1602 from the control MS and process MS data function 1606 are the lookup and transmission back to the external interfaces manager 1602 of the instrument MS data and MS signature library data 1612. In addition, the mass spectrometer data analyzer 1608 communicates with the external interfaces manager 1602, allowing it to monitor the mass spectrometer data analysis and mass spectrometer analyzed data. Also, a message concerning the instrument health status is communicated to the external interfaces manager 1602 from the maintain the health of instrument function 1610.

The control and monitor instrument cycles function 1604 manages and controls the operational cycles previously described and illustrated in FIG. 14, including setting valve positions, heater controls, temperatures and the timing parameters associated with each cycle. In addition to the communications already discussed, this function serves to communicate a request for power from the various devices to the power and vacuum manager 1600, a request for the instrument self-test and status from the maintain health of instrument function 1610 and to provide for control of the mass spectrometer 18 by means of its communication with the control MS and process MS data function 1606.

Information concerning the substance to be analyzed is input into the control and monitor instrument cycles function 1604 which then communicates that information into the mass spectrometer 18 by means of its communication to the control MS and process MS data function 1606. The control and monitor instrument cycles functions 1604 also receives data from the instrument mass spectrometer data and mass spectrometer signature library data 1612 used to set up a library search algorithm for single-ion monitoring or multiple ion monitoring detection modes. A mass spectrometer status is also communicated to the control and monitor instrument cycle functions 1604 from the control MS and process MS data function 1606.

The MS control and processing function 1606 controls the mass spectrometer system, including calibration and synchronization of the ion source accelerating voltage, electrostatic analyzer voltage and ion detector output in order to produce and calibrate the resulting mass spectra. The control MS and process MS data function 1606 can also access the instrument mass spectrometer data and mass spectrometer signature library data 1612 to perform real-time processing and matching mass spectra to the library. That same function 1606, in addition to the communication paths described above, provides to the maintain health of instrument function 1610 an indication of the health status of the mass spectrometer 18. The control MS and process MS data function 1606 receives a communication from the maintain health of instrument function 1610 for protecting the operation of the mass spectrometer 18 in the event of a system or power failure and also communicates with the analyzed mass spectrometer data function 1608.

The mass spectrometer data analyzer 1608 provides the analytical routines required to fully analyze the mass spectral data collected as a result of the operation of function 1606. This function 1606 incorporates the mass spectral analyses functions generally found in commercial workstations previously cited. Under function 1606, the mass spectral data may be processed in real-time or may be stored for later analyses under the function 1608 analytical programs. The mass spectrometer data analyzer 1608 is also connected to access the instrument mass spectrometer data and mass spectrometer signature library 1612 to perform matching of unknown mass spectra. In addition, the mass spectrometer data analyzer function 1608 functions to protect the data analysis under control of the maintain health of instrument function 1610.

Each of these functions of the system software is further described below in the context of operation of the mass spectrometer system 10.

The mass analyzer system must always be under a high vacuum that is in the range of $10^{-5}$ Torr. or better in order to operate. To ensure that the vacuum is maintained, not only during system operation but also during periods when the main spectrometer system 10 is either on the shelf or in a standby mode, the present design provides for continuous power to the on-board ion pump 42 which is an autonomous vacuum protection feature of the instant system. The power is provided by an on-board battery supply 202 which is rechargeable from standard 110 volts, 50–60 cycle AC current. It is not necessary to turn on the computer 24 or otherwise exercise manual control over the mass spectrometer system 10 for this vacuum protection feature to operate. It is always on.

A warning circuit is also provided which will provide an audio alarm if the system 10 is plugged into a power outlet which is not operating at the time so that, during storage periods, since a loss of AC power over a long enough time period could eventually cause the battery supply 202 to run down with a subsequent eventual loss of vacuum, a signal is generated to alert the operator. A loss of vacuum condition is non-recoverable in terms of the packaged system 10 itself. If a loss of vacuum condition occurs, an external roughing pump is needed for which a connection is provided and the system would then have to be restarted by roughing the system and then starting up the ion pump 42 again.

When the mass spectrometer system 10 is initially started up upon completion of its construction or at a central servicing depot, in the preferred embodiment, a roughing pump external to the system 10 is utilized. A valve is then closed which connects that external system to the internal vacuum envelope 20 and the system is maintained at $10^{-5}$ to $10^{-7}$ Torr. vacuum with the internal ion pump. The roughing pump is then disconnected. Once the ion pump is functioning, the system is autonomous and it functions automatically. There is also a protective circuit as part of the vacuum protection for the system 10 which, if there is a reduction in the voltage in the battery supply 202, will turn off other power draining devices within the system 10 and will retain as long as possible the power to the ion pump 42 simultaneously with providing a low voltage warning to the operator that battery voltage is dropping. As described, before the system 10 is turned on, it operates in an autonomous mode without operator intervention.

The turn-on sequence for operating the system 10 involves first turning on the computer 24. The computer system 24 is the heart of the operator-to-instrument interface and therefore all operations, selections of operating cycles and control options by the operator are exercised through the microcomputer 24 with the one exception of the autonomous vacuum control system described above.

Operator communication with the computer 24 is accomplished with a keyboard entry and a visual display which provides guidance to the operator by means of menus to assist in defining the keyboard options for the operator, the system status and also for display of data system functions. Thus the display acts as a multi-function subsystem. During the initial turn-on sequence after the computer is brought up, the system goes through a self-check routine which has a number of functions, most importantly among them being the check for ion source 34 performance. The first ion source 34 performance test is a check for filament continuity, the filament 1228 being one of the crucial parts of the ion source 34. The operation of the high voltage power supplies 30 which power the ion source 34 and the electric sector 36 is then checked. The other circuit which is checked at start-up is the high voltage power supply 30 to the ion detector 44 which is also a crucial operating circuit to the operation of the mass spectrometer 18.

The system 10 also contains a number of solenoid latching valves 212, 1402-1412 and 1416, and the position of each one of those valves is checked to ensure that they are in the pre-operational position. Those valve positions ensure that the sampling subsystem is closed off and that the ion source inlet 914 is closed off, in order to preclude possible contamination during quiescent or at rest periods between sampling cycles.

The next step after turn-on is to perform a system calibration. The primary function of the calibration is to validate the relationship between the sweep potential on the ion source 34 or the accelerating voltage from the ion source 34 and the mass values to be assigned to signals in the mass spectrum. By mass value assignments is meant taking the mass spectrum and calibrating the X axis to determine that at this point, the mass to charge ratio is a particular value. It functions to assign a scaling factor to the horizontal or X axis for the mass spectrometer 18.

The system calibration process involves a calibration gas which is stored on board the system 10. A momentary release of the calibration gas into the ion source 34 of the mass spectrometer 18 with consequent production of a mass spectra is used for the calibration. The mass spectra is generated by a standard sweep and values of the voltages that generate the sweep are compared with the position of the key masses of the ions of the calibrate gas. Any variation from the expected predetermined positions is used to recalculate the sweep voltages and thereby to correct for any small variations that may occur because of temperature, misalignment or other changes in the many subsystems which form the mass spectrometer portion 18 of the system 10.

In order to perform this calibration function, the calibrate signature and also the characterization of the sweep voltage is stored on-board the system lo. The sweep voltage is a decreasing exponential voltage from approximately 3,000 to 150 volts at the upper scale of the mass. The calibrate signature is contained in an EPROM 1504 that is part of each system 10 and contains calibrate signature information unique to each system 10. It is determined at the completion of manufacturing of each system in the course of the checkout and test of each unit in order to account for small variations in manufacturing tolerances and possible idiosyncrasies in each one of the mass spectrometers 18.

In addition to start-up, the calibrate cycle can be run at any time if there is any question in the operator's mind concerning the accuracy of the system 10. In normal operation, the system 10 will remain in calibration for prolonged periods, that is periods of days. However, as a precaution, depending on the circumstances of age and storage of the system 10, a calibration run at the beginning of each day's operation would typically be performed, but during usage, the operator will determine what is best.

There are four other cycles subject to user executable commands under function key or keyboard control, in addition to the calibrate basic operating cycle of the system 10. The first operating cycle is direct MS. In that operating cycle, an atmospheric sample is brought into the membrane separator 16a. It is introduced into the system 10 through an atmospheric inlet 228 which is protected by an in-line filter to keep particulates and other contamination out of the inlet line. A small water vapor extractor operates after the in-line filter to reduce the water vapor content of the sample before it is actually brought into the membrane separator 16a.

The function of the membrane separator 16a is to use the selective permeability of the membrane to allow sample molecules, which are typically organics, to selectively permeate the membrane at a much greater and higher rate than the background gas such as nitrogen and oxygen present in the atmosphere. The sample concentration produced by the membrane separator 16a is typically three orders of magnitude greater in favor of the organic sample molecules than at its input. The sample then enters the ion source 34 and the normal scanning of the mass spectrometer 18 occurs.

When sample molecules come in through the membrane separator 16a to the ion source 34, they are introduced via an inlet tube 914 and the higher vacuum on the other side of that tube to the block 1202 of the ion source 34. The block 1202 provides a passageway for the sample molecules into an ionization chamber which is the heart or the center of the block assembly 1102. In normal operation, the block 1202 is heated by a heating element 1232 which is controllable within the range of 50° to 200° temperature of the block 1202 so that the block is normally held isothermal at an elevated temperature which is selected by the operator. The block 1202 is heated in order to avoid plating out or adsorption of the sample molecules onto the metal surface of the block. The block 1202 is also gold-plated in order to reduce that reactivity and the possibility of sample plating.

The sample molecules then enter the ionization chamber, at which time the electron gun contained in the ion source 34 establishes a beam of electrons, the energy of which are about 70 electron volts. The electron beam interacts with the sample molecules in a known fashion to create positive ions and ion fragments of organic molecules in a way that is also well known in the art.

The magnetic field in the ion source 34, which causes the electron trajectories to be helical and thereby improve the ionization efficiency and increased path length, is provided by a cylindrical magnet 1220 which is integral to the block assembly 1102. The cylindrical magnet 1220 surrounds the ionization chamber. It has a slot cut in it at an angle which is predetermined, in order to account for second order effects of the electric and magnetic fields on the electron trajectory, at an angle of approximately 6°.

In the ionization chamber, the ion fragments that are created by the electron impact are moved toward the extraction lens 1114 by a repeller assembly 1214 which is located inside the cylindrical magnet 1220 that forms the body of the ionization chamber. The repeller assembly 1214 is a two-piece assembly, the front surface of which is shaped to match the electric field lines established inside of the ionization chamber. The electrons in this region create positive ions which are then repelled into the effective region of the saddle lens 1114.

The saddle lens 1114 provides the extracting potential to bring the ions out of the ionization chamber and transmit them to the first element of the accelerating lens system, the split lens 1112. Each of the lenses in the accelerating lens system has an independent separate potential. The split lens 1112 allows for the tuning of the mass spectrometer system 18 and will permit the ion beam to be redirected so that it is optimally focused on the entrance slit 1106 to the mass spectrometer system 18, which is the next lens element.

The entrance slit 1106 provides the initial focus of the ion beam in the instant double focusing mass analyzer system 21. It establishes the point of departure for the ion beam through the remainder of the mass analyzer 21. The ion beam next is shaped by a lens system 1104 that includes an ion current monitor. The ion current monitor collects a fixed fraction of the ion beam that has been created and is passing through the entrance slit 1106 and provides an indication of the total number of ions that are being created at any one time in the source. This is important because it allows feedback to other elements of the mass spectrometer system 18.

One such element is the inlet valve that would permit the mass spectrometer system 10 to shut down the inlet to the ion source 34 and (the inlet of the sample to the membrane separator) in order to avoid sample overload conditions in which the vacuum pump 22 might not be able to handle the total amount of sample. Thus, by sensing an excessive ion current at lens 1104, the feedback to the inlet 914 to protect the ion source 34 and the vacuum in the instrument is possible or can be automatically performed by the system 10 as programmed.

There are also two other uses of this total ion current. The first is that it is recorded and is part of the spectrum that is available in the data system to permit a plot of total ion current for a given GC/MS run. A second use of the total ion current is to vary the gain on the ion detector 44 in order to accommodate wide swings in sample concentration and to ensure that the ion detector gain is matched to the ion signal that is present.

After the lens system 1104 the ions then proceed or are accelerated and continue through the entrance shunt 1110. The entrance shunt 1110 is a grounded slit which provides a termination for the electric field that is created by the inner and outer segments of the electric sector. By shunting that field, the fringe field effects that would otherwise perturb and spread and change the quite precisely defined ion beam are reduced. The entrance and exit shunts 1110 and 908, respectively, at both ends of the electric sector provide termination points for the electric field and also eliminate any fringe field effects on the ion beam.

As described, the positive ions are accelerated through the combination of lenses, forming a beam, and than enter the electric sector 36 through the entrance shunt 1110. The ion bean enters the electric section 36 in the region between the two electric sector plates 1300a and 1300b. The electric sector plates 1300 provide a radial and highly homogeneous electric field which acts on the positive charged ion fragments in accordance with the generally known principles of electrodynamics. In order to accelerate the charged particles along a circular path, the magnitude of the energy of the incoming ion fragments and the electric field will determine the preferred trajectory along the center line of the plates 1300, so that, by varying the potential on the plates 1300 in a fixed ratio with the accelerating potential of the ion source 34, varying energies can be selected to pass through the electric sector 36 and the exit shunt 908.

At the exit of the electric sector 36 there is another primary focal point 910 which is used to align the electric sector/ion source combination. The physical alignment of the in connection with the mounting of the electric sector 36 and the construction details of the ion source 34 and their relationship to each other constructed in the manner described herein, the amount of electrical tuning that is necessary is minor in order to ensure that the ion beam is focused at the exit of the electric sector 36.

The ions then pass into a field-free region where they are not accelerated. The ions coast until they enter the region in which the magnetic field produced by the magnet analyzer 40 is present. Whereas the electric field produced by the electric sector 36 is radial, the magnetic field produced by the magnetic analyzer 40 is in the z direction, that is, it is vertical out of the page. In accordance with generally known principles of electrodynamics, a charged particle in a magnetic field will also be accelerated. In the present mass analyzer 21, the magnetic field is fixed and thus always acts as a momentum filter that produces the result that since the velocity of the particle has been determined by the accelerating potential and the further refinement of that potential in the electric sector 36, the only variable then in the system is the mass of the ions. Changing the velocity will change the mass which is on the preferred centerline trajectory through the magnet 40 to the exit slit 908.

In that manner, the accelerating potential of the ion source 34 and the matching potential on the electric sector 36 creates the mass spectrum by changing the mass-to-charge ratio of those ions which reach the magnetic analyzer 40 exit slit.

On the other side of the exit slit there is an ion detector 44 which can be one of several types. When the ions exit the magnet 40, there is some separation before they actually reach the primary focal point which is the exit slit. The ion detector 44 is thus located on the other side of the exit slit. The ion detector 44 has a sensitive surface which emits electrons when a charged particle impacts it and the accelerating field in the ion detector 44 then amplifies the ion current, which is the number of ions that are impacting the surface per unit of time, and that amplified signal is then converted from its raw analog form to a digitized signal by an A/D converter 1522. The digitized signal is then stored and used in the data analysis features of the instrument.

The mass spectrometer system 10 of the present invention is capable of operating in four different cycles or modes. Of course, additional modes are also possible. The first is the direct MS mode, which would normally be used to determine whether a particular compound was present in the atmosphere that was being sampled, rather than to perform a complex analysis of the atmosphere. This is so because in a direct MS mode all compounds that might be present in the sample will create ions in the mass spectra and a full analysis of that mass spectra is an extremely complex analytical task. On the other hand, if a search is being made for one compound, by reference to the signature library for direct MS sampling, the system 10 can determine the one or two principle ions which are characteristic of that compound and look only for those ions. The presence of those ions is used to indicate the presence of the compound whose existence is being sought.

In this mode, the operator is normally asking the question whether the compound X is present. In the direct MS mode, the operator has several choices to be made and inputted into the system 10. One is the choice of the compound that he is looking for. The second choice is the duration of the sampling process that he wants to use to look for the compound. Typically that is the time period during which the on-board sampling pump 206 will be drawing an atmospheric sample through the atmospheric inlet system 228 described previously, past the membrane separator 16a and then out. The sampling pump 206 is used to draw the sample past the membrane 16a. As shown in FIG. 14 and described in connection therewith, there is a series of valves which open and close under computer 24 control, depending upon the choice by the operator of the sample cycle. This system brings together a variety of what would normally be present in a separate system or be manually transferred from point a to point b. Since an analytical grade mass spectrometer and supporting analyzing and operating subsystems have been brought together into an integrated package by the present system, the operator can, by a simple keyboard function, make that choice.

In the direct MS mode, the sample is introduced through the appropriate valving system past the membrane separator 16a by the pump 206 and then pumped out of the system 10. By choice of the compound that the operator is looking for, the system will go into the appropriate library which is unique to the selected cycle and look for the characteristic ions and the ion source temperature to use in order to identify that particular sample.

In this direct MS sampling mode, instead of using a sweep of the full mass range of the mass spectrometer system 18, the ion source accelerating voltage is set only at the voltage appropriate to specific characteristic ions. One or two characteristic ions may be used, depending on the nature of the material under test and how characteristic a single ion may be. Such operation is normally referred to as single ion monitoring or a SIM mode, which is well known in the mass spectrometer art. If a detection is made, then an audible alarm is provided that alerts the operator to the detection.

The second operating cycle is essentially the same as the direct MS mode with the exception that an enrichment cycle is provided which permits the mass spectrometer 10 to look for much more dilute samples than in the direct MS mode. The cycle for the enriched MS requires that the operator select the amount of enrichment time, that is the time in which the enrichment or concentration cartridge 214 will actually be accepting a sample flow. Thus in the enrichment MS cycle, the enrichment cartridge 214 is part of the loop through which the sample is passed, as described in connection with FIG. 14. The atmospheric sample is brought into the system 10 through the enrichment cartridge 214 by the operation of the sampling pump 206. At the completion of the time selected by the operator for sampling, the system 10 will automatically close the sampling inlet valve 1402, close the sampling valve 1406, open the carrier gas cartridge 200, which is provided with the system 10 and, will cold flow the carrier gas through the system for approximately one second to clear the atmospheric sample out. The system 10 then will thermally desorb the sample from the enrichment cartridge 214 onto the membrane separator 16a, where the rest of the sampling takes place. The same lookup library is used as with the direct MS mode.

In addition, a choice of carrier gases can be provided. In the preferred embodiment, the system 10 would utilize helium, but it is also possible to use either hydrogen or nitrogen.

The gas chromatograph 14 is also thermally programmable, so that the operator can establish the initial temperature and the final temperature and a heating rate for the GC cycle.

In the third cycle, the enriched GC/MS mode, the sampling phase through the cartridge 214 is the same as that described in connection with the enriched MS mode. In the enriched GC/MS mode, however, after the sample is thermally desorbed, it flows to the gas chromatograph 14 and then to the membrane separator 16a. That allows the system 10 to produce a careful and detailed analysis of the composition of the sample to be tested. In this mode, the question the operator normally asks is "what compound(s) is present?" Through the use of a full GC/MS analysis the system to is able to determine the compounds that are present in an atmospheric sample. For this mode, a different on-board lookup library is utilized. That library uses a full sweep in order to determine the whole mass range.

The fourth mode is a manually assisted cycle in which the sample is prepared off line through any one of several known techniques and extracted into a solvent which is then used to transport the sample into the system 10. This manual technique involves use of a syringe, which is introduced into the injection port 216 through a waxy plug contained in the port. The injection port 216 is heated by a heater 1422. The heated injection port 216 evaporates the solvent into the GC carrying the sample. As shown in FIG. 26, the injection port 216 is accessible to the outside of the system 10. A guide is provided in the injection port 216 in order to guide the needle of the syringe.

The operation of the gas chromatograph 14 then proceeds using the carrier gas as described in connection with cycle 3, with the mass spectrometer 18 running a full sweep. The determination typically to be made is what is present, as opposed to, is x present? in the first two modes. Using this mode, samples can be extracted from water or from soil. It is also possible to extract samples from biological fluids, using methods which are generally well known to the art. For such GC/MS runs, the data that is gathered is digitized and is stored for each sweep of the mass analyzer 21.

As described in cycles 3 and 4, the operator normally will be interested in the determination of what compounds are present. In order to make that determination, the stored data will be referred to the on-board data analysis program which does a library search between the spectra that is obtained on these runs and the stored library signature using a library lookup algorithm similar to those which are well known in the art. That library search then will result in potential matches between stored signatures in the library and the unknown signature of the unknown compound. The best three matches will be shown to the operator by means of the flat display screen, if there are in fact three which satisfy the criteria. If there are more than three, just the best three will be presented. However, the raw data is always available and can be extracted to an external storage medium either by a direct cable connection or modem to an external computer 1520 either using telemetry or a modem, as appropriate.

The system 10 also permits the operator to display in graphical form the mass spectra for any of the particular scans associated with a particular compound at choice of the operator. It also permits a visual comparison between the library signature and the unknown scans for verification of the match, again at the choice of the operator. It is also possible for the operator to call up a total ion chromatogram, which is well known in the art as an alternate form of data.

The operator also has the flexibility of designating runs for storage in a suitable memory device or removable media. Each run is automatically tagged with a time and date which is built into the clock of the system 10. There is also a choice of on-board signature libraries which are available that can be read in from an external source. Customized libraries for compounds that are of specific interest to a particular operator and are likely to be encountered by that operator can also be provided.

Although only a preferred embodiment is specifically illustrated and described herein, it will be appreciated that many modifications and variations of the present invention are possible in light of the above teachings and within the purview of the appended claims without departing from the spirit and intended scope of the invention.

What is claimed is:

1. An analytical grade mass spectrometer system for testing a sample, said mass spectrometer system being contained in a single enclosure, comprising:
    an analytical grade mass spectrometer, capable of achieving a resolution of greater than 1 AMU and having a mass range of greater than 100 AMU and which provides an output signal representative of the characteristics of said sample under test;

a gas chromatograph;

a sample inlet and concentrator assembly for interfacing said analytical grade mass spectrometer with said gas chromatograph;

a vacuum housing for containing said analytical grade mass spectrometer within a vacuum environment of at least $10^{-5}$ Torr;

means for maintaining said vacuum in said vacuum housing;

control means contained within said enclosure for operating and monitoring said analytical grade mass spectrometer;

means for processing the output signal from said analytical grade mass spectrometer in order to produce a representation of the mass spectrum characteristics of said sample under test; and said single enclosure having an internal volume of less than one cubic yard.

2. A self-contained analytical grade mass spectrometer system for testing a sample, said mass spectrometer system being contained in a single enclosure, comprising:

a vacuum housing contained in said single enclosure;

a double focussing analytical grade mass analyzer contained in said vacuum housing and having a resolution of greater than 1 AMU and a mass range of greater than 200 AMU and which provides an output signal representative of the characteristics of said sample under test;

a gas chromatograph;

a sample inlet and concentrator assembly for interfacing said double focussing analytical grade mass analyzer with said gas chromatograph;

signal processing and control means for processing said output signal produced by said mass spectrometer system and for controlling the operation of said mass spectrometer system, said signal processing and control means being contained in said single enclosure;

input/output means connected to said signal processing means for inputting data and information to and receiving data and information from said signal processing means and control means, said input/output means being contained in said single enclosure means;

said single enclosure means having an internal volume of one cubic yard or less and weighing, together with said analytical grade mass spectrometer system, less than 300 hundred pounds; and wherein said analytical grade mass spectrometer system has a power consumption of less than 500 watts.

3. A mass analyzer assembly for use with an analytical grade mass spectrometer system for testing a sample, said mass analyzer assembly serving to provide alignment of an ion beam produced by said mass spectrometer, comprising:

means for producing a source of ions from said sample under test and for focussing said produced ions into a focussed ion beam;

means connected to said means for producing said source of ions for subjecting said focussed ion beam to a radial electric field;

means for magnetically deflecting said focussed ion beam into an ion beam detecting means after said ion beam has been subjected to said radial electric field;

means for producing a vacuum such that said ion beam is always under vacuum; and wherein said vacuum producing means further comprises unitary means for aligning at least any two of the following: (1) said source of ions, (2) said means for producing said radial electric field, (3) said means for producing said magnetic deflection of said ion beam, and (4) said ion beam detecting means.

4. An electric sector for use in a mass analyzer assembly of a mass spectrometer system, comprising:

a mounting plate;

a pair of electrically conductive sector plates insulatingly mounted to said mounting plate in such a manner that said pair of sector plates are aligned parallel to each other and perpendicular to said mounting plate; and each of said mounting plate and said pair of sector plates have a plurality of corresponding holes formed therein, in which a like plurality of spheres are positioned in order to provide said alignment and ensure said electrical insulation between said mounting plate and each of said pair of sector plates.

5. A self-contained portable analytical grade mass spectrometer system for testing a sample, said mass spectrometer system being contained in a single enclosure, comprising:

a vacuum housing contained in said single enclosure;

a double focussing analytical grade mass analyzer contained in said vacuum housing and having a resolution of greater than 1 AMU and a mass range of greater than 200 AMU and which provides an output signal representative of the characteristics of said sample under test;

a gas chromatograph;

a sample inlet and concentrator assembly for interfacing said double focussing analytical grade mass analyzer with said gas chromatograph;

signal processing and digital data processing means for processing said output signal produced by said mass spectrometer system and for controlling the operation of said mass spectrometer system, said signal processing and control means being contained in said single enclosure;

input/output means connected to said signal processing means for inputting data and information to and receiving data and information from said signal processing means and control means, said input/output means being contained in said single enclosure means;

said single enclosure means having an internal volume of one cubic yard or less and weighing, together with said analytical grade mass spectrometer system, less than 300 pounds; and wherein said analytical grade mass spectrometer system has a power consumption of less than 500 watts.

6. An analytical grade gas chromatograph/mass spectrometer system housed in an easily transportable single enclosure, comprising:

a digital data processor for controlling an operation of said gas chromatograph/mass spectrometer system and for processing spectra obtained by said system;

a sample collection and sample introduction system;

a temperature-controlled gas chromatograph being electrically connected to said digital data processor for controlling the temperature and sample flow through said gas chromatograph;

said sample collection and sample introduction system being connected to said temperature-controlled gas chromatograph by a plurality of different sample pathways which provides a plurality of sample introduction modes for said gas chromatograph/mass spectrometer system;

an analytical grade mass spectrometer which includes a primary vacuum pump and has a mass range of greater than 200 amu;

a mass spectrometer interface assembly connected between said gas chromatograph and said mass spectrometer, said mass spectrometer interface being electrically connected to said digital data processor for control of its temperature and sample flow; and wherein said digital data processor forms an integral part of said analytical grade gas chromatograph/mass spectrometer system and provides control of the operation of said mass spectrometer, said gas chromatograph, said sample collection and sample introduction system and said mass spectrometer interface assembly, under programmed control and with keyboard entry by a user.

7. The gas chromatograph/mass spectrometer system of claim 6, wherein said plurality of different sample pathways of said sample collection and sample introduction system utilizes a plurality of valving means under control of said digital data processor to achieve said plurality of sample introduction modes.

8. The gas chromatograph/mass spectrometer system of claim 6, wherein said gas chromatograph includes means for providing active cooling under control of said digital data processor.

9. The gas chromatograph/mass spectrometer system of claim 6, wherein said mass spectrometer interface comprises a dual inlet system permitting sample entry from said single collection and sample introduction system and said gas chromatograph and whose output is connected to said mass spectrometer.

10. The gas chromatograph/mass spectrometer system of claim 9, wherein at least one of said inlets is a direct inlet from said sample collection and sample introduction system to said mass spectrometer interface.

11. The gas chromatograph/mass spectrometer system of claim 6, wherein said mass spectrometer interface comprises a single membrane interface.

12. The gas chromatograph/mass spectrometer system of claim 6, wherein said primary vacuum pump is an ion pump and wherein said gas chromatograph/mass spectrometer system includes a battery for maintaining that ion pump in a constantly powered state, even during periods when said gas chromatograph/mass spectrometer system is turned off.

13. The gas chromatograph/mass spectrometer system of claim 6, wherein said analytical grade mass spectrometer is a double focussing mass spectrometer having a unitary alignment mechanism.

14. The gas chromatograph/mass spectrometer system of claim 13, wherein said analytical grade mass spectrometer utilizes a magnet means which provides a magnetic field for pumping an ion pump used for maintaining the vacuum pressure of said mass spectrometer and for an analyzer magnet assembly.

15. The gas chromatograph/mass spectrometer system of claim 14, wherein said magnet means includes a magnetic yoke which acts as a shield for said ion pump and which forms a part of a vacuum enclosure which surrounds said mass spectrometer.

16. A sample collection and sample introduction system for an analytical grade gas chromatograph/mass spectrometer system for providing a plurality of sample introduction modes into said gas chromatograph/mass spectrometer system, comprising:

a digital data processor for controlling said sample collection and sample introduction system;

an injector port for receiving a sample to be analyzed by said gas chromatograph/mass spectrometer system, said injector port including a heating means connected to be controlled by said digital data processor for providing thermal desorption of said sample;

a concentrator port for receiving said sample to be analyzed by said gas chromatograph/mass spectrometer system, said concentrator port including a heating means connected to be controlled by said digital data processor for providing thermal desorption of said sample;

an atmospheric inlet for receiving an atmospheric sample to be analyzed by said gas chromatograph/mass spectrometer system;

a membrane separator connected between said concentrator port and said atmospheric inlet and the mass spectrometer of said gas chromatograph/mass spectrometer system;

a sampling pump connected to provide a source of suction through said membrane separator; and a plurality of sampling lines and sampling valves connected between each of said injector and concentrator ports, said atmospheric inlet, said sampling pump and said membrane separator, the operation of said valves being controlled by said digital data processor.

17. The sample collection and sample introduction system of claim 16, wherein said sampling lines and said valves are temperature controlled under control of said digital data processor.

18. The sample collection and sample introduction system of claim 16, wherein said sampling lines and valves provide a first sample path from said atmospheric inlet to said membrane separator in a direct MS cycle mode.

19. The sample collection and sample introduction system of claim 16, wherein said sampling lines and valves provide a second sample path from said atmospheric inlet through said concentrator part and to said membrane separator in an enriched MS cycle mode.

20. The sample collection and sample introduction system of claim 16, wherein said sampling lines and valves provide a third sample path from said injector port through said gas chromatograph to said membrane separator in a direct injection cycle mode.

21. The sample collection and sample introduction system of claim 16, wherein said sampling lines and valves provide a fourth or enriched MS/GC cycle mode.

22. The sample collection and sample introduction system of claim 16, wherein said plurality of sample introduction modes are automatically executed by said sample collection and sample introduction system under programmed control by said digital data processor.

23. The sample collection and sample introduction system of claim 16, wherein said membrane separator provides a direct membrane inlet into said mass spectrometer of said gas chromatograph/mass spectrometer system.

* * * * *